US012629193B2

(12) United States Patent
Korman

(10) Patent No.: US 12,629,193 B2
(45) Date of Patent: May 19, 2026

(54) SYSTEMS AND METHODS FOR METATARSAL PHALANGEAL JOINT FUSION

(71) Applicant: WRIGHT MEDICAL TECHNOLOGY, INC., Memphis, TN (US)

(72) Inventor: Zachary Korman, St. Louis, MO (US)

(73) Assignee: WRIGHT MEDICAL TECHNOLOGY, INC., Memphis, TN (US)

( * ) Notice: Subject to any disclaimer, the term of this patent is extended or adjusted under 35 U.S.C. 154(b) by 40 days.

(21) Appl. No.: 18/782,076

(22) Filed: Jul. 24, 2024

(65) Prior Publication Data

US 2025/0049489 A1     Feb. 13, 2025

Related U.S. Application Data

(60) Provisional application No. 63/518,594, filed on Aug. 10, 2023.

(51) Int. Cl.
| | |
|---|---|
| *A61B 17/88* | (2006.01) |
| *A61F 2/46* | (2006.01) |
| *A61B 17/56* | (2006.01) |
| *A61B 90/00* | (2016.01) |
| *A61F 2/30* | (2006.01) |

(52) U.S. Cl.
CPC ........ *A61B 17/8872* (2013.01); *A61F 2/4606* (2013.01); *A61B 2017/564* (2013.01); *A61B 2090/3966* (2016.02); *A61F 2002/30622* (2013.01)

(58) Field of Classification Search
CPC ............ A61B 17/1775; A61B 17/8872; A61B 2017/564; A61B 2017/565; A61B 2090/3966; A61F 2/4606
See application file for complete search history.

(56) References Cited

U.S. PATENT DOCUMENTS

| | | | | |
|---|---|---|---|---|
| 7,763,027 | B2 * | 7/2010 | Irving .................. | A61B 17/157 |
| | | | | 606/88 |
| 9,220,518 | B2 * | 12/2015 | Neal ...................... | A61B 17/15 |
| 9,387,313 | B2 * | 7/2016 | Culbert .............. | A61B 17/1757 |
| 10,413,306 | B2 * | 9/2019 | Russell .............. | A61B 17/8897 |
| 10,555,757 | B2 * | 2/2020 | Dayton ............... | A61B 17/151 |
| 10,849,663 | B2 * | 12/2020 | Dayton .................. | A61B 17/15 |
| 11,020,130 | B2 * | 6/2021 | Patel .................. | A61B 17/1717 |
| 11,076,896 | B2 * | 8/2021 | Schreiber ........... | A61B 17/1703 |
| 11,147,590 | B2 * | 10/2021 | Dayton .............. | A61B 17/6416 |
| 11,439,413 | B2 * | 9/2022 | Bederson ........... | A61B 17/1695 |
| 11,672,549 | B2 * | 6/2023 | Cundiff .............. | A61B 17/1775 |
| | | | | 606/87 |
| 11,701,133 | B2 * | 7/2023 | McGinley ............. | A61F 2/4202 |
| | | | | 606/87 |
| 11,918,236 | B2 * | 3/2024 | Patel .................. | A61B 17/1782 |
| 12,185,958 | B2 * | 1/2025 | Korman ............... | A61B 17/17 |
| 12,329,393 | B2 * | 6/2025 | Carlo ................. | A61B 17/1728 |
| 2014/0180348 | A1 * | 6/2014 | Thoren ................. | A61B 17/17 |
| | | | | 606/86 R |
| 2017/0196574 | A1 * | 7/2017 | Fallin ................. | A61B 17/1775 |

(Continued)

*Primary Examiner* — Anu Ramana

(74) *Attorney, Agent, or Firm* — DUANE MORRIS LLP

(57) ABSTRACT

A system for metatarsal phalangeal joint fusion includes a hinged guide; a trajectory guide attachable to the hinged guide; and an anchoring wire to attach the hinged guide to a bone.

22 Claims, 25 Drawing Sheets

(56) References Cited

U.S. PATENT DOCUMENTS

| | | | |
|---|---|---|---|
| 2020/0093501 A1* | 3/2020 | Patel .................. | A61B 17/1717 |
| 2020/0281637 A1* | 9/2020 | Denham ............... | A61F 2/0805 |
| 2023/0013727 A1 | 1/2023 | Korman et al. | |
| 2023/0052337 A1* | 2/2023 | Carlo, III ........... | A61B 17/1633 |
| 2023/0053657 A1 | 2/2023 | Korman et al. | |
| 2023/0157712 A1* | 5/2023 | Patel .................. | A61B 17/1717 |
| | | | 606/96 |

* cited by examiner

P

MT

DTP

PTD

P

MT

DTP

PTD

SYSTEMS AND METHODS FOR METATARSAL PHALANGEAL JOINT FUSION

CROSS REFERENCE TO RELATED APPLICATIONS

This application claims the benefit of U.S. Provisional Patent Application No. 63/518,594, filed Aug. 10, 2023, the entire contents of which is incorporated by reference for all purposes as if fully set forth herein.

FIELD OF DISCLOSURE

The present disclosure relates to bone fastener drill targeting guide systems and methods that can be used in surgical procedures for fusing metatarsal phalangeal (MTP) joints.

BACKGROUND

Metatarsal phalangeal (MTP) joints are the joints where the foot bones join the toes (i.e., the middle part or 'ball' of a foot). A first MTP joint fusion is a surgical procedure to fuse a distal portion of the first metatarsal bone to a proximal portion of the proximal phalanx bone to stiffen the first MTP joint in an effort to eliminate pain caused by arthritis or another deformity that leads to difficulty in walking, running, and wearing shoes. In a first MTP joint fusion procedure, a portion of the toe joint is removed and the bones are joined (fused) together permanently to relieve pain and swelling so the patient can walk more comfortably. This procedure also removes any motion at the big toe joint.

During a MTP joint fusion surgical procedure, the first phalanx bone is separated from the metatarsal bone and the joint cartilage is removed from the bone. The metatarsal and phalanx are realigned and then fixed in relation with two fasteners. K-wires are traditionally used to hold the phalanx bone and the metatarsal head at the intended translated position during the subsequent fastener fixation procedure.

In a minimally-invasive MTP Fusion procedure, it is difficult to gain sufficient access to the MTP joint to prepare it for fusion, to maintain exact bone positioning intraoperatively while placing implant fixation, and to place a biomechanically optimal implant construct repeatably. Conventionally, manual techniques are used for gaining phalanx-metatarsal distraction, for holding the bones in a desirable relative position, and for placing fixation fasteners (usually screws if done minimally invasively). It is difficult to place these fasteners repeatably across multiple procedures, and to ensure they do not intersect with each other. Therefore, a guiding instrument for setting the trajectory of k-wires and fixation fasteners is desired.

SUMMARY

To overcome the problems described above, embodiments of the present disclosure provide the following advantages: (i) systems with a cannulated portion for initial placement with a stabilizing wire in the metatarsal head, (ii) radiopaque indicators for alignment (including parallax confirmation), (iii) two sets of converging bone anchoring wires, (iv) linear distraction and compression of the MTP joint via a lead screw, (v) selectable and lockable dorsiflexion per surgeon preference, (vi) adjustable varus-valgus, (vii) multiple trajectory options for each implant fastener throw, (viii) prong indicator to show multiple implant fastener trajectory options at once on x-ray (including parallax confirmation), (ix) ability to drill and place implant fasteners through a locked hinged guide while maintaining bone positioning, and (x) predetermined implant fastener trajectory options that do not intersect each other.

According to an embodiment, a system for metatarsal phalangeal joint fusion includes a hinged guide; a trajectory guide attachable to the hinged guide; and an anchoring wire to attach the hinged guide to a bone.

In an aspect, the hinged guide includes: a connecting body; a hinge body attached to and hinged with respect to the connecting body; a metatarsal guide attached to the hinge body; and a phalanx guide attached to the connecting body via a dowel and a lead screw.

In an aspect, the hinged guide further includes: a first set screw to adjust articulation between the connecting body and the hinge body; and a second set screw to adjust articulation between the hinge body and the metatarsal guide.

In an aspect, the hinged guide includes radiopaque indicators.

In an aspect, a distance between the connecting body and the phalanx guide is adjustable via the lead screw.

In an aspect, the trajectory guide includes: an upright portion that is insertable into the hinged guide; and an indicator portion that extends from the upright portion.

In an aspect, the indicator portion includes at least two radiopaque indicators that extend parallel to each other.

The system can further include a single-chamfer wire sleeve configured to be inserted through a hole in the hinged guide along a trajectory for a fixation fastener.

In an aspect, the hinged guide includes: a connecting body; a metatarsal guide attached to and hinged with respect to the connecting body; and a phalanx guide attached to the connecting body via a dowel and a lead screw.

The system can further include a first knob to lock articulation between the connecting body and the metatarsal guide.

The system can further include two first converging anchoring wires insertable through the phalanx guide and into a phalanx; and two second converging anchoring wires insertable through the metatarsal guide and into a metatarsal.

The system can further include an outrigger to attach the trajectory guide to the phalanx guide.

The system can further include a second knob to lock articulation between the connecting body and the outrigger.

The system can further include an adjustment screw to adjust elevation between the connecting body and the outrigger.

The system can further include an outer single-chamfer wire sleeve configured to be inserted through a hole in the outrigger and anchored into a bone via a spike protruding from one end of the outer single-chamfer wire sleeve.

The system can further include an inner single-chamfer wire sleeve configured to be inserted through a bore of the outer single-chamfer wire sleeve and guide a fastener guide wire into a bone.

In an aspect, a bore through the outer single-chamfer wire sleeve is offset from a center of the outer single-chamfer wire sleeve.

According to another embodiment, a method of fusing a metatarsal phalangeal joint incudes anchoring a hinged guide to a phalanx or a metatarsal of the metatarsal phalangeal joint; aligning the hinged guide with the phalanx or the metatarsal; distracting the phalanx and the metatarsal; preparing the metatarsal phalangeal joint; adjusting dorsiflexion of the metatarsal phalangeal joint; locking the hinged guide to set the dorsiflexion; compressing the phalanx and the metatarsal; selecting a trajectory of a fixation fastener; and inserting the fixation fastener into one of the phalanx and the metatarsal along a selected trajectory.

In an aspect, the anchoring includes placing a guide wire into about a center of a metatarsal head and placing the hinged guide over the guide wire.

In an aspect, the anchoring includes placing two first converging wires through the hinged guide and into the phalanx and two second converging wires through the hinged guide and into the metatarsal.

In an aspect, aligning the hinged guide includes visualizing radiopaque indicators in the hinged guide.

In an aspect, the selecting a trajectory of a fixation fastener includes adjusting a trajectory guide with respect to the metatarsal phalangeal joint.

In an aspect, the selecting a trajectory of a fixation fastener includes selecting a diameter of the fixation fastener.

The above and other features, elements, characteristics, steps, and advantages of the present invention will become more apparent from the following detailed description of preferred embodiments of the present invention with reference to the attached drawings.

BRIEF DESCRIPTION OF THE DRAWINGS

The inventive concepts of the present disclosure will be described in more detail in conjunction with the following drawing figures. The structures in the drawing figures are illustrated schematically and are not intended to show actual dimensions.

DETAILED DESCRIPTION

Figure 1:
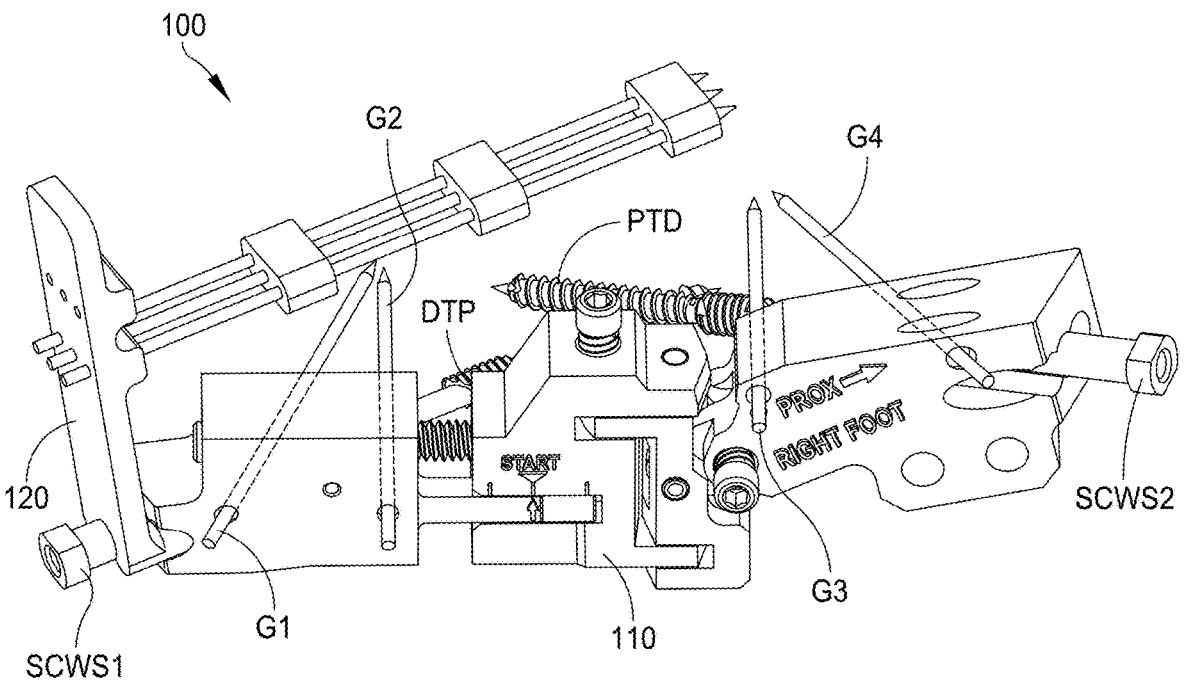
FIG. 1 shows a system for metatarsal phalangeal (MTP) joint fusion according to an embodiment of the present disclosure.

This description of the exemplary embodiments is intended to be read in connection with the accompanying drawings, which are to be considered part of the entire written description. The drawing figures are not necessarily to scale and certain features may be shown exaggerated in scale or in somewhat schematic form in the interest of clarity and conciseness. In the description, relative terms such as "horizontal," "vertical," "up," "down," "top" and "bottom" as well as derivatives thereof (e.g., "horizontally," "downwardly," "upwardly," etc.) should be construed to refer to the orientation as then described or as shown in the drawing figure under discussion. These relative terms are for convenience of description and normally are not intended to require a particular orientation. Terms including "inwardly" versus "outwardly," "longitudinal" versus "lateral" and the like are to be interpreted relative to one another or relative to an axis of elongation, or an axis or center of rotation, as appropriate. Terms concerning attachments, coupling and the like, such as "connected" and "interconnected," refer to a relationship wherein structures are secured or attached to one another either directly or indirectly through intervening structures, as well as both movable or rigid attachments or relationships, unless expressly described otherwise. When only a single machine is illustrated, the term "machine" shall also be taken to include any collection of machines that individually or jointly execute a set (or multiple sets) of instructions to perform any one or more of the methodologies discussed herein. The term "operatively connected" is such an attachment, coupling or connection that allows the pertinent structures to operate as intended by virtue of that relationship. In the claims, means-plus-function clauses, if used, are intended to cover the structures described, suggested, or rendered obvious by the written description or drawings for performing the recited function, including not only structural equivalents but also equivalent structures.

Unless otherwise expressly stated, it is in no way intended that any method set forth herein be construed as requiring that its steps be performed in a specific order, nor that with any apparatus, specific orientations be required, unless specified as such. Accordingly, where a method claim does not actually recite an order to be followed by its steps, or that any apparatus claim does not actually recite an order or orientation to individual components, or it is not otherwise specifically stated in the claims or description that the steps are to be limited to a specific order, or that a specific order or orientation to components of an apparatus is not recited, it is in no way intended that an order or orientation be inferred, in any respect. This holds for any possible non-express basis for interpretation, including: matters of logic with respect to arrangement of steps, operational flow, order of components, or orientation of components; plain meaning derived from grammatical organization or punctuation, and; the number or type of embodiments described in the specification.

A system for metatarsal phalangeal (MTP) joint fusion 100 according to a first embodiment of the present disclosure is shown in FIG. 1. The system 100 is used to align (i) anchoring wires to be placed into the metatarsal and phalanx bones forming the MTP joint for stabilization, (ii) the metatarsal and phalanx bones for fusion, and (iii) fixation fasteners. The system 100 can include a medial guide 110, a trajectory guide 120 including three prongs, at least anchoring wires G1-G4, single-chamfer wire sleeves SCWS1 and SCWS2, a distal-to-proximal fastener DTP (through the phalanx P and into the metatarsal MT), and a proximal-to-distal fastener PTD (through the metatarsal MT and into the phalanx P).

Figure 2:
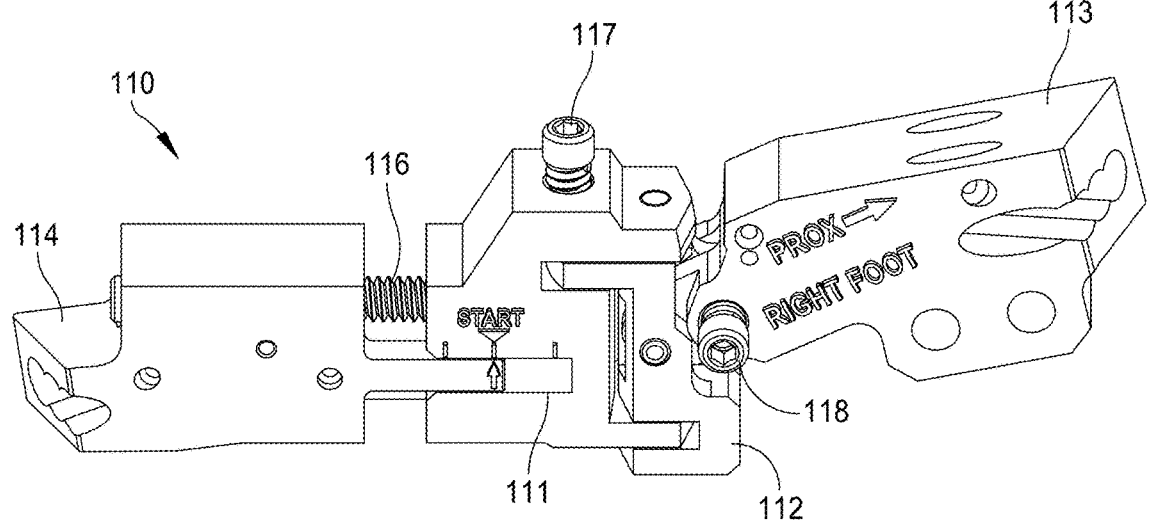
FIG. 2 shows portions of a medial guide.

FIG. 2 shows portions of the medial guide 110 and their relative orientations to each other. As shown, the medial guide 110 can include a connecting body 111, a hinge body 112, a metatarsal guide 113, a phalanx guide 114, a dowel 115 (not visible), a lead screw 116, a first set screw 117, and a second set screw 118. The connecting body 111, the hinge body 112, the metatarsal guide 113, and the phalanx guide 114 can be made of a plastic or polymer and can include radiopaque indicators (ROI) on or within these components. A radiopaque indicator or marker can be used with medical imaging such as X-ray, CT, fluoroscopy, etc. to provide a reference or identify a point of interest. Further details of the individual components are included in the operation description below.

Figure 3:
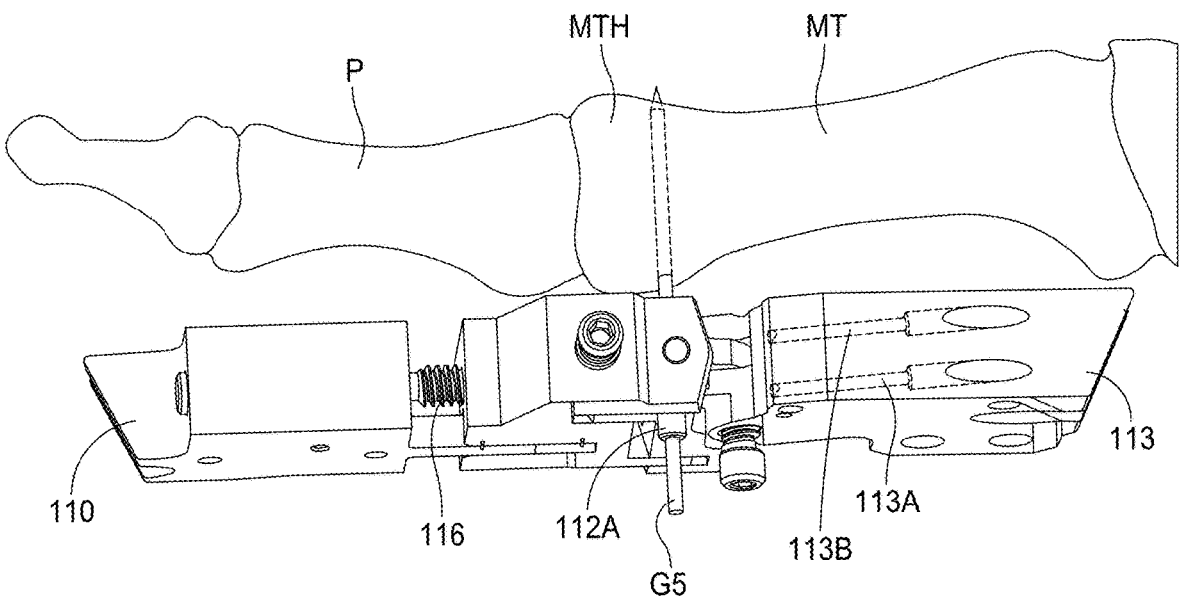
FIG. 3 shows the medial guide alongside a metatarsal and a phalanx to be fused.

The system 100 has multiple features that allow it to aid in performing the entire MTP fusion procedure. The perspective view of FIG. 3 shows the medial guide 110 alongside a metatarsal MT and a phalanx P to be fused. First, a guide wire G5 is placed medially-laterally in about the center of the metatarsal head MTH at the same distal-proximal level as the sesamoids. The medial guide 110 is placed over the guide wire G5 through a cannulated hinge 112A of the hinge body 112 and alongside the first metatarsal MT and the phalanx P. The metatarsal guide 113 can include two ROIs 113A and 113B to align the proximal end of the medial guide 110 with the metatarsal central axis (in a lateral view). The lead screw 116 can be used as a ROI to align the distal end of the medial guide 110 with the phalanx center axis (in a lateral view) Distal-proximal alignment with the MTP joint can be verified with the ROI 119 indicated in FIG. 2. During initial guide placement, this ROI 119 would be aligned with the MTP joint space in the lateral view. The proximal set of indicators 113A, 113B are doubled to provide a parallax indicator to ensure the imaging viewing plane is aligned with the metatarsal guide 113 and the imaging is providing accurate information.

Figure 4:
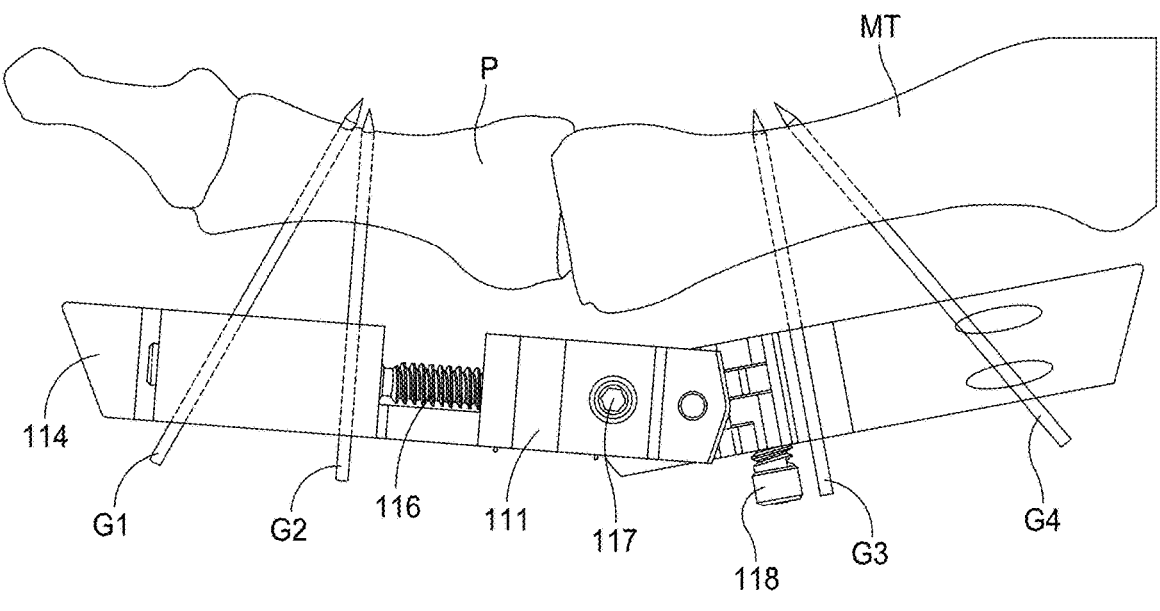
FIG. 4 and FIG. 5 are views showing two converging anchoring wires placed in each of the phalanx and the metatarsal.
Figure 5:
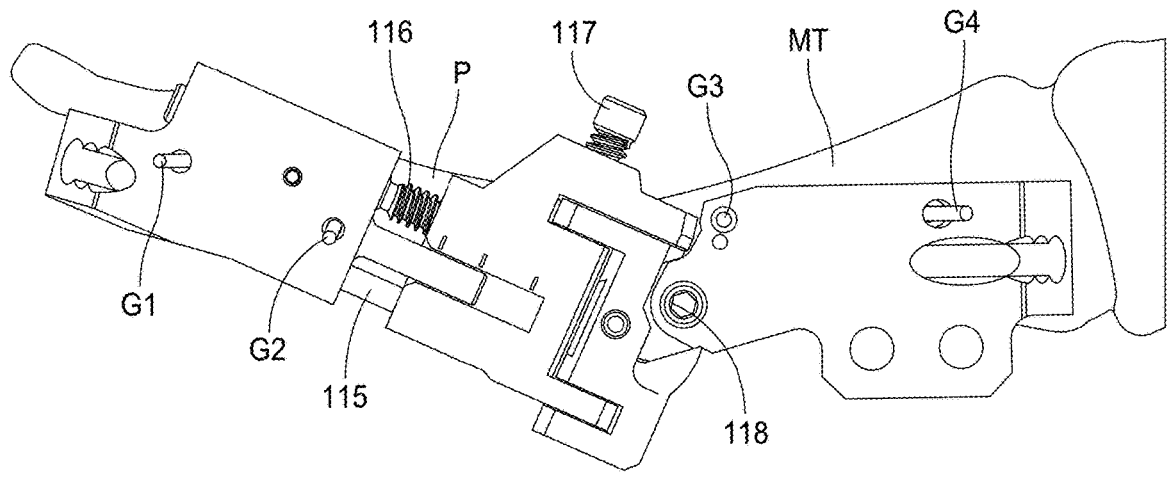
Figure 6:
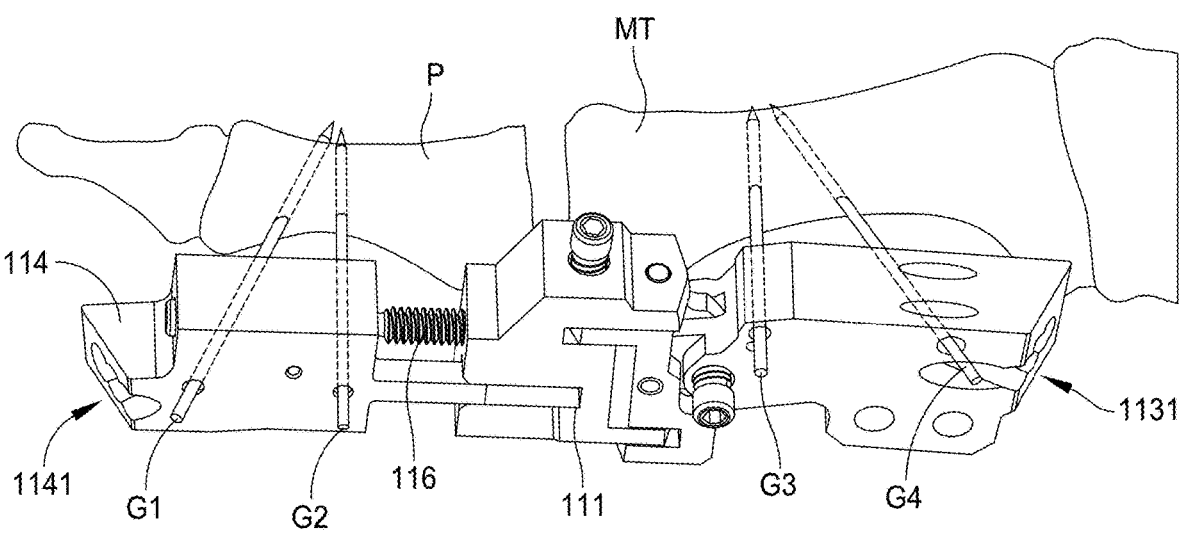
FIG. 6 shows the anchored phalanx distracted from the metatarsal.

FIG. 4 is a top view and FIG. 5 is a side view showing that two converging anchoring wires G1 and G2 (e.g., 1.6 mm diameter) can then be placed in the phalanx P and two converging anchoring wires G3 and G4 (e.g., 1.6 mm diameter) can then be placed in the metatarsal MT. The guide wire G5, shown in FIG. 3 can be removed. The first set screw 117 and the second set screw 118 can lock the medial guide 110 from articulation. With the set screws 117, 118 locked, and after incision at the MTP joint, distraction of the phalanx P and the metatarsal MT is now possible via the lead screw 116 and dowel 115 (not visible in FIG. 4) mechanism. For example, a tool such as screw driver, Allen wrench, or hex driver (e.g., 2.5 mm Hex driver) can be used to rotate the lead screw 116 and force the phalanx guide 114 away from the main body 111. In this manner, as shown in FIG. 6, the anchored phalanx P will be distracted from the metatarsal MT. This action opens the MTP joint to facilitate preparing the MTP joint for fusion (i.e., removal of cartilage and fenestration of subchondral cortical surface). To gain access to the plantar aspect of the metatarsal head MH, the second (dorsiflexion) set screw 118 can be loosened, and the phalanx P can be plantarflexed.

Figure 27:
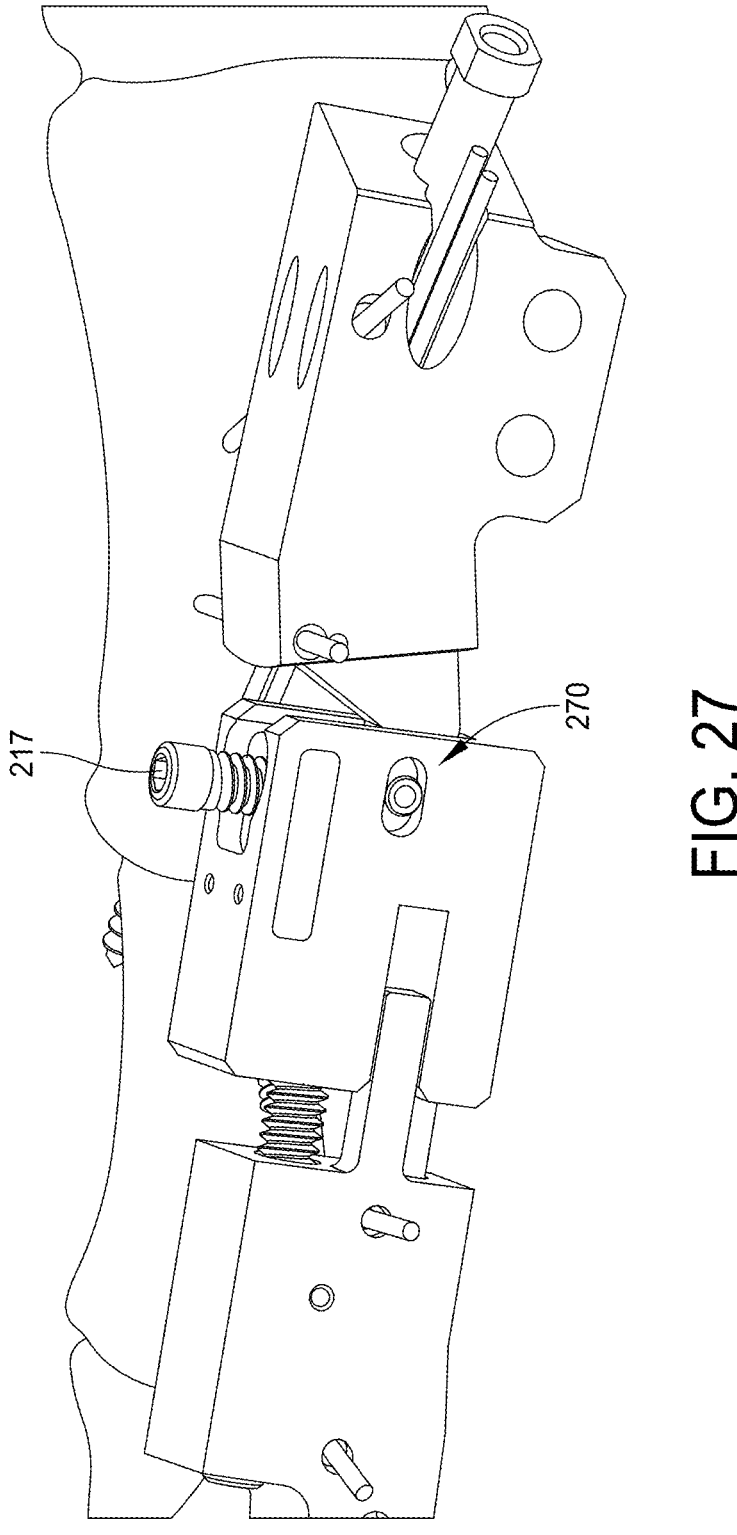
FIG. 27 shows a medial guide with a ball joint mechanism.

Once MTP joint preparation is complete, the final selection of desired dorsiflexion can be arranged and locked via the second (dorsiflexion) set screw 118. Compression of the phalanx P and the metatarsal MT can now be achieved drawing together the same lead screw 116 and dowel 115 mechanism. If necessary, varus/valgus adjustment can be performed using the first (dorsally oriented valgus) set screw 117 prior to full compression. The medial guide 110 can remain in place stabilizing the correction arrangement for the remainder of the procedure. Optionally, varus/valgus and dorsiflexion adjustments can be combined using one a restricted ball joint mechanism and locked simultaneously. For example, as shown in FIG. 27, a dowel-in-slot mechanism can be used to keep the ball of the ball joint 270 from rotating in a pronation/supination direction, as this is an undesirable degree of freedom. So with this restriction, the ball joint 270 only has two degrees of freedom remaining, which matches the two degrees of freedom found in medial guide 110 that can be locked by set screws 117 & 118. Similarly, the ball joint 270 can be locked by set screws 217.

Figure 7:
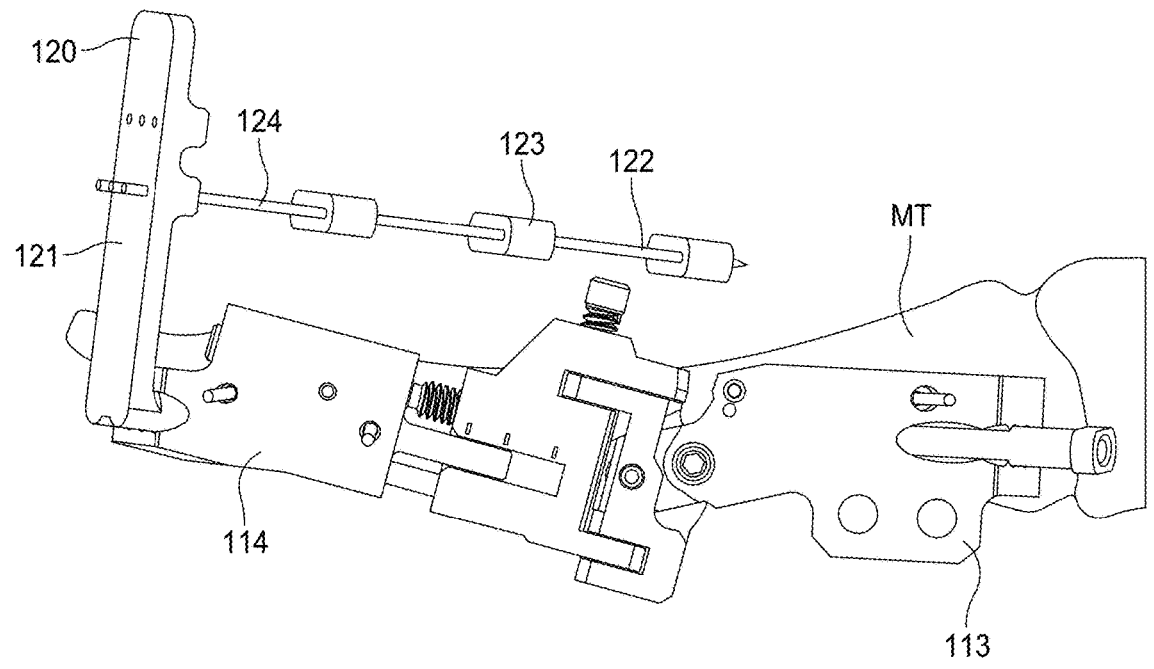
FIG. 7 and FIG. 8 show a three-prong trajectory guide inserted into a phalanx guide.

The three-prong trajectory guide 120 can then be first inserted into either a three-hole slot 1141 in the phalanx guide 114, as shown in FIG. 7, or a three-hole slot 1131 in the metatarsal guide 113 and used to select between trajectory options for a distal-to-proximal fastener DTP (through the phalanx P and into the metatarsal MT) and a proximal-to-distal fastener PTD (through the metatarsal MT and into the phalanx P). Once the first fastener, DTP or PTD, is in place, the three-prong trajectory guide 120 can be moved to the other three-hole slot 1131 or three-hole slot 1141 and the second fastener can be inserted after a trajectory is selected between the options provided by the three-prong trajectory guide 120.

The three-prong trajectory guide 120 can include an upright portion 121 that is insertable and extends from the three-hole slot 1131, 1141, and an indicator portion 122 that extends perpendicular from the upright portion 121 above the MTP joint. The upright portion 121 can be defined to include a right angle, or any other suitable angle, that extends from a portion inserted into the three-hole slot and then to a vertical elongated portion. The vertical elongated portion can include at least one set of adjacent holes used to hold the indicator portion 122. The at least one set of holes can be at various distances from an end of the vertical elongated portion and provide options in which to insert the indicator portion 122.

The indicator portion 122 can include at least one spacer block 123 and ROIs 124 as that extend through a set of holes in the upright portion and through the spacer block 123. The distances between the set of holes in the elongated portion and the spacer block 123 can be the same so that the ROIs 124 extend parallel to each other, as shown in the top view of FIG. 8. More than one spacer block 123 can be used to secure and align the ROIs 124. As shown, the three-prong trajectory guide 120 can include a configuration with three ROIs 124, but other amounts are possible. The alignment of these ROIs 124 and ROIs in the portion of the three-prong trajectory guide 120 that is insertable into the three-hole slots 1131, 1141 define a parallax indicator.

Figure 8:
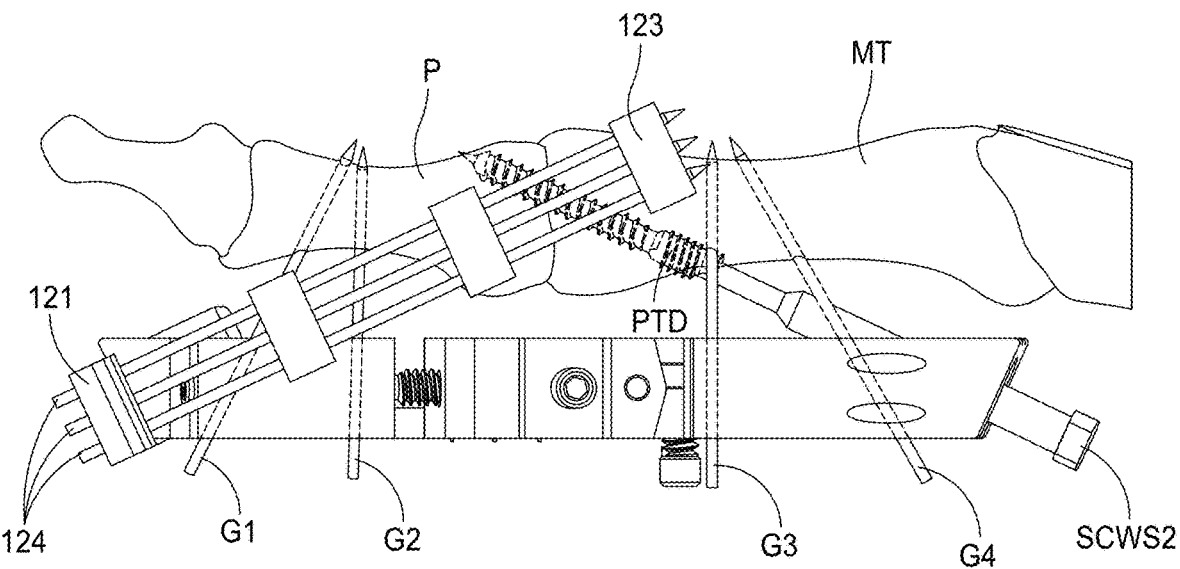
Figure 9:
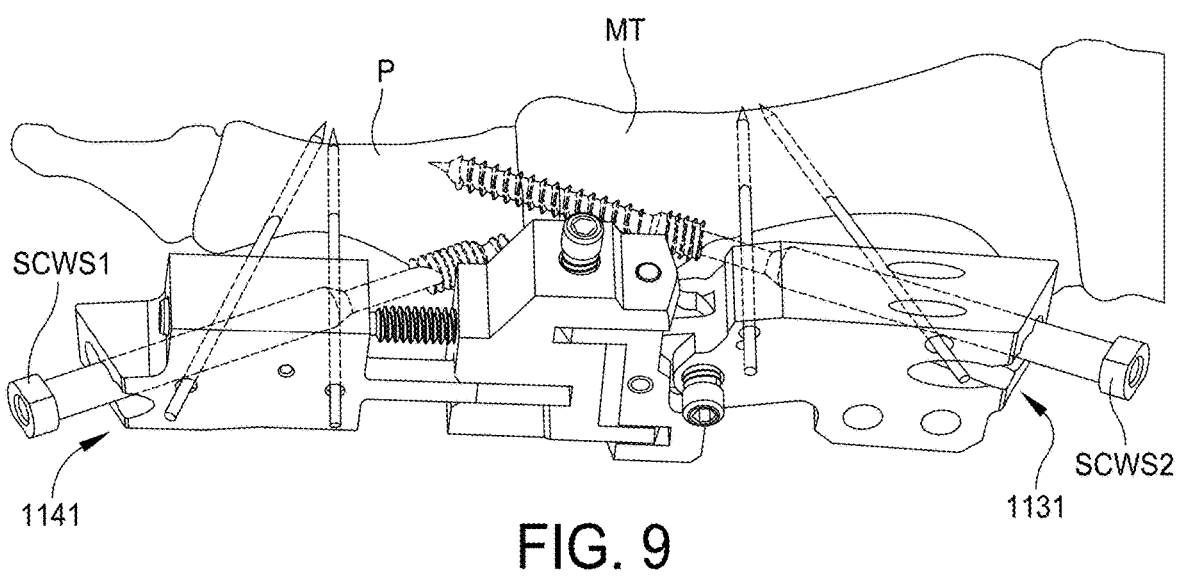
FIG. 9 shows single-chamfer wire sleeves in place.

FIG. 8 shows when the x-ray plane and the three-prong trajectory guide 120 are aligned properly, the ROIs 124 overhanging the MTP joint show three separate and parallel trajectories where a fastener can be placed in the bones. Once a surgeon selects which trajectory to follow, the three-prong trajectory guide 120 is removed from the medial guide 110, a small incision is made at the fastener insertion point near the MTP joint, a single-chamfer wire sleeve SCWS (FIG. 8 show one single-chamfer wire sleeve SCWS2 in place) is inserted through the hole of the three-hole slot 1131, 1141 that corresponds to the selected trajectory and down to bone, and a fastener guide wire is placed though the single-chamfer wire sleeve. Depth gauging, pre-drilling, and driving the DTP or PTD fastener implant can happen through the selected hole of the three-hole slot after the single-chamfer wire sleeve SCWS is removed. Although FIG. 8 shows the both the single-chamfer wire sleeve SCWS2 and the PTD fastener both concurrently in place, during the procedure, the single-chamfer wire sleeve SCWS2 would be removed prior to insertion of the PTD fastener. This process is repeated with the other set of three trajectory hole options, which were carefully positioned such that they do not intersect with the first set of selected trajectories. FIG. 9 shows single-chamfer wire sleeves SCWS1 and SCWS2 in place in the selected holes of the corresponding three-hole slots 1131, 1141. Once the DTP and PTD fasteners are in place, the medial guide 110 can then be removed.

Figure 10:
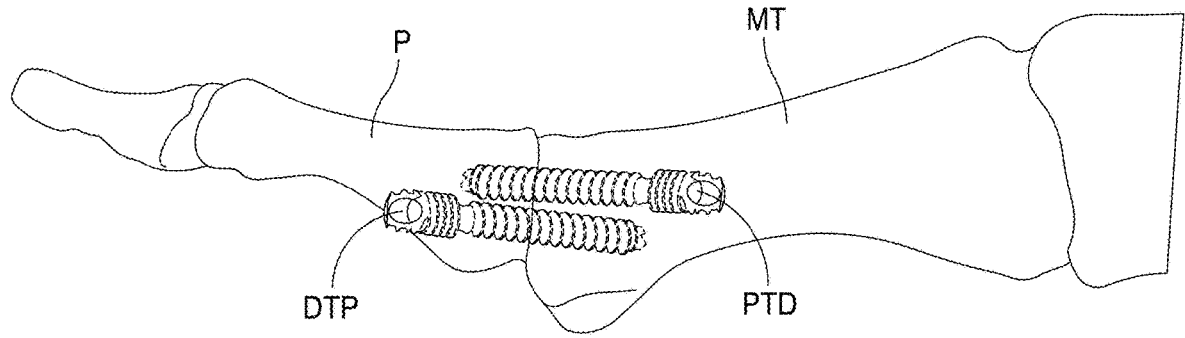
FIG. 10 and FIG. 11 show the result of a MTP fusion procedure.
Figure 11:
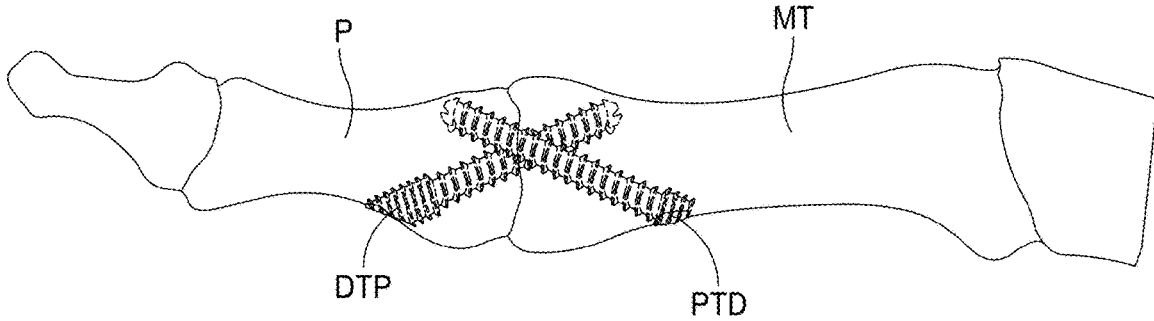

FIGS. 10 and 11 show the result of the MTP fusion procedure. FIG. 10 is a side view and FIG. 11 is a top view of the MTP joint showing the DTP and PTD fasteners in place.

Figure 12:
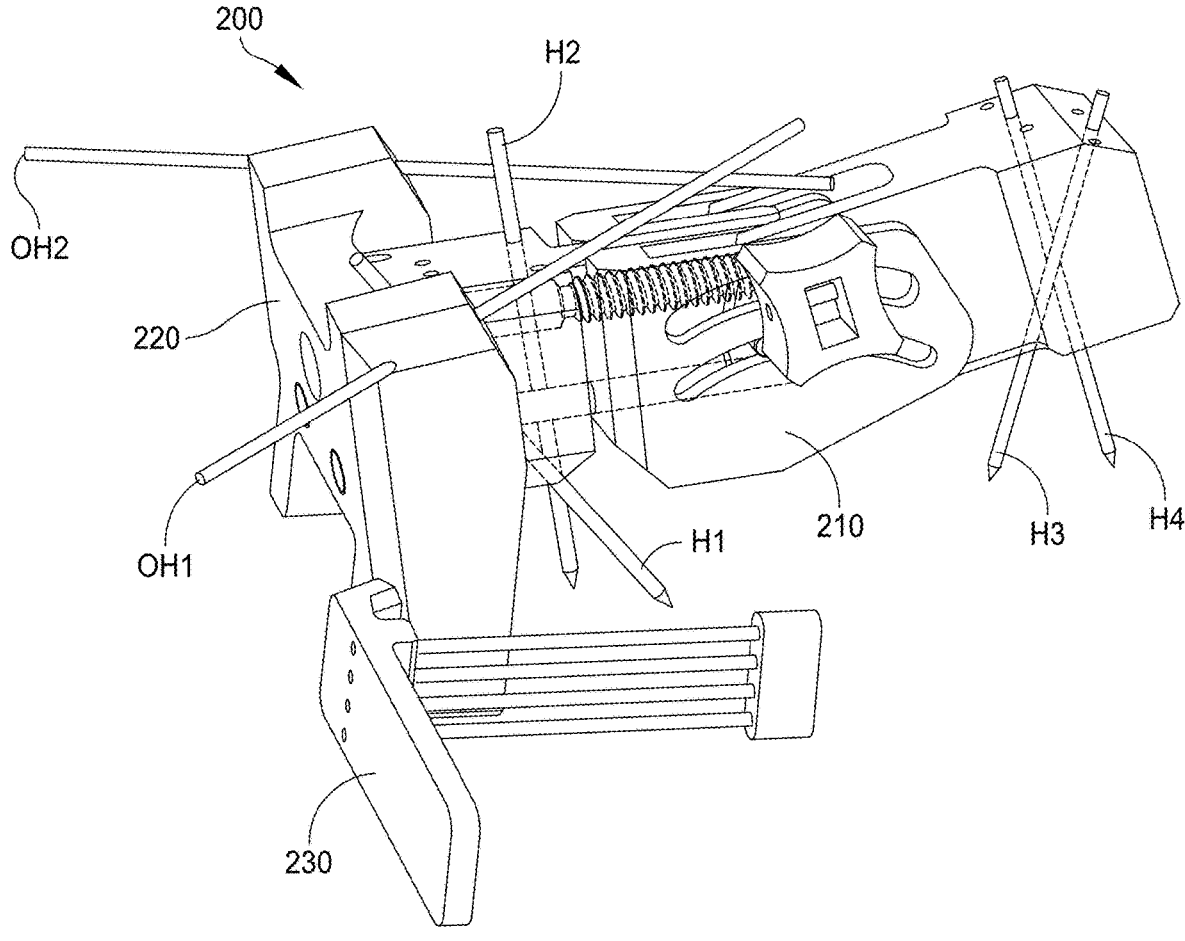
FIG. 12 shows a system for MTP joint fusion according to another embodiment of the present disclosure.

A dorsal system for metatarsal phalangeal (MTP) joint fusion 200 according to a second embodiment of the present disclosure is shown in FIG. 12. The system 200 is used to align (i) anchoring wires to be placed into the metatarsal and phalanx bones forming the MTP joint for stabilization, (ii) the metatarsal and phalanx bones for fusion, and (iii) fixation fasteners. The system 200 can include a dorsal guide 210, an outrigger 220, a pronged trajectory guide 230, overhanging wires OH1, OH2, and anchoring wires H1 to H4.

Figure 13:
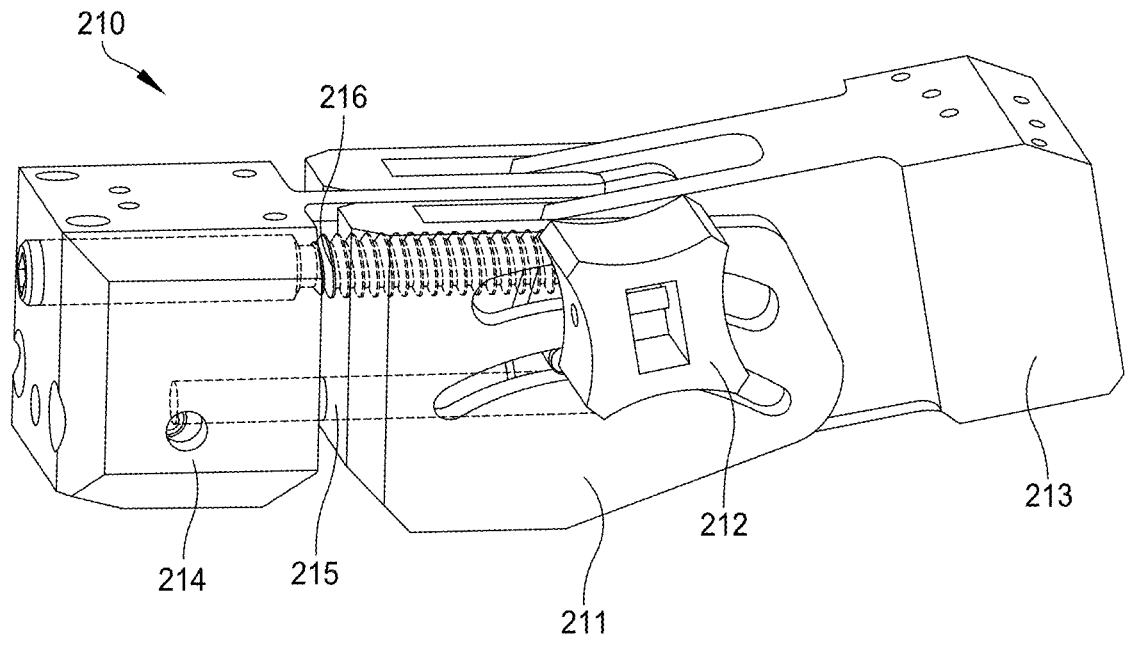
FIG. 13 shows portions of a dorsal guide.

FIG. 13 shows portions of the dorsal guide 210 and their relative orientations to each other. As shown, the dorsal guide 210 can include a connecting body 211, a knob 212, a metatarsal guide 213, a phalanx guide 214, a dowel 215, and a lead screw 216. The connecting body 211, the knob 212, the metatarsal guide 213, and the phalanx guide 214 can be made of a plastic or polymer and can include radiopaque indicators (ROI) on or within these components. Further details of the individual components are included in the operation description below.

Figure 14:
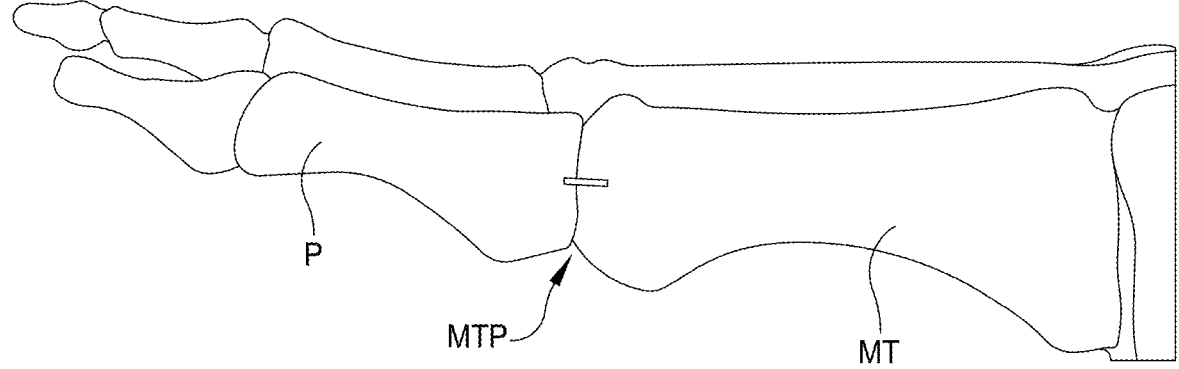
FIG. 14 shows a medial incision of a MTP joint to be fused.
Figure 15:
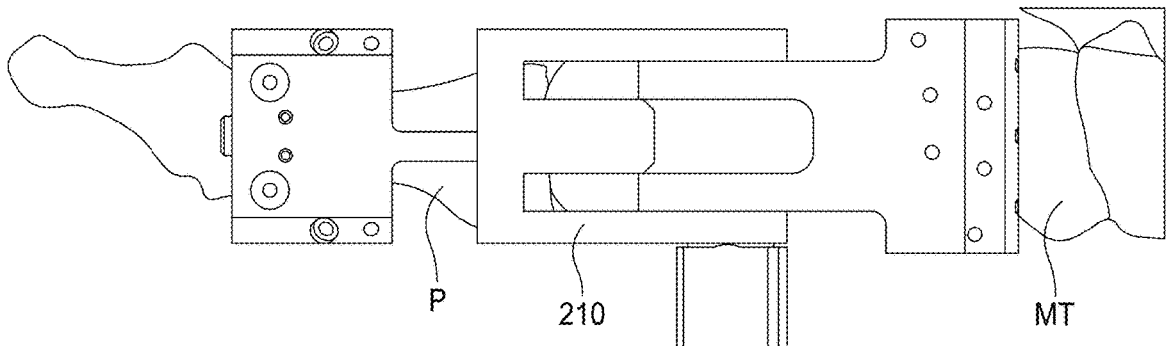
FIG. 15 shows the dorsal guide over a metatarsal and a phalanx to be fused.
Figure 16:
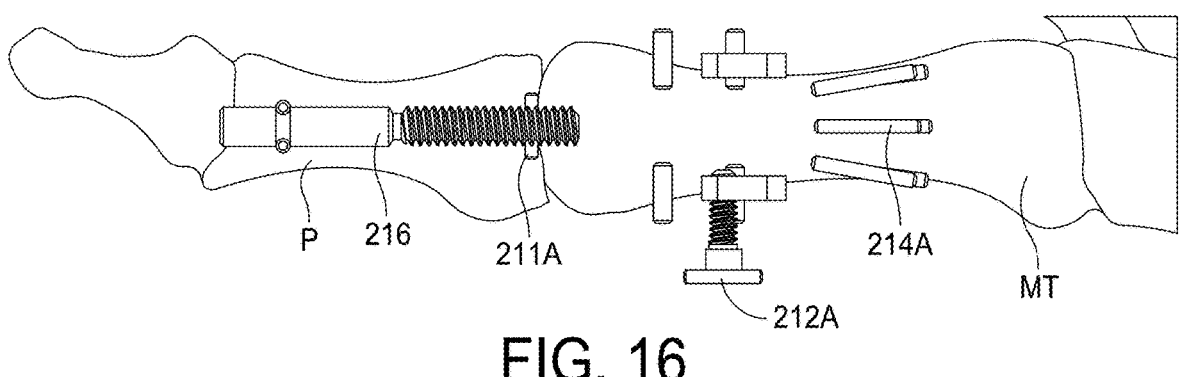
FIG. 16 shows locations of radiopaque indicators in FIG. 15.
Figure 17:
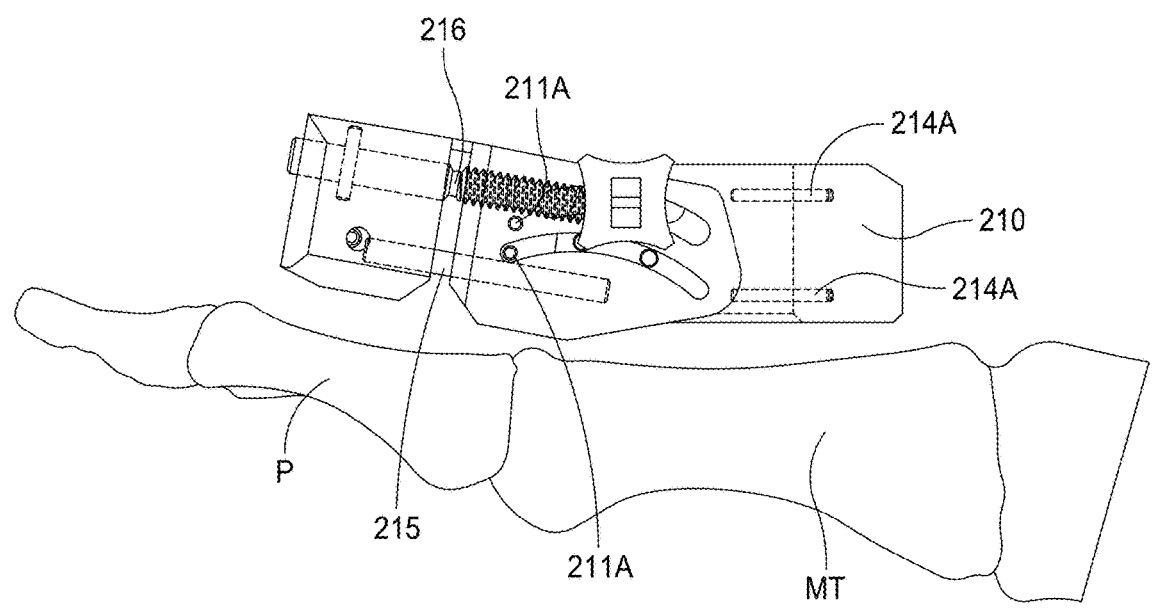
FIG. 17 is a side view of the dorsal guide over a metatarsal and a phalanx to be fused.

The system 200 has multiple features that allow it to aid in performing the entire MTP fusion procedure. As shown in FIG. 14, first, an incision is made, indicated by the line at the MTP joint, and the MTP joint is released from a medial approach. The dorsal guide 210 is then placed over the first metatarsal MT and phalanx P, as shown in the top view of FIG. 15 and the side view of FIG. 17. The top view of FIG. 16 and the side view of FIG. 17 show locations of radiopaque indicators and other non-indicating radiopaque components of FIG. 15 (with portions of the dorsal guide 210 omitted for clarity) including 211A, 212A (i.e., the knob hardware), 214A, and 215/216 (aligned such that 215 is not visible behind 216) to align the distal end with the phalanx central axis, the distal-proximal position with the MTP joint space, and the proximal end with the metatarsal central axis. Manual reduction of any present hallux valgus is possible in this step. Each set of radiopaque indicators is "doubled" to provide a parallax indicator to ensure the x-ray viewing plane is aligned with the dorsal guide 210 and providing accurate information.

Figure 18:
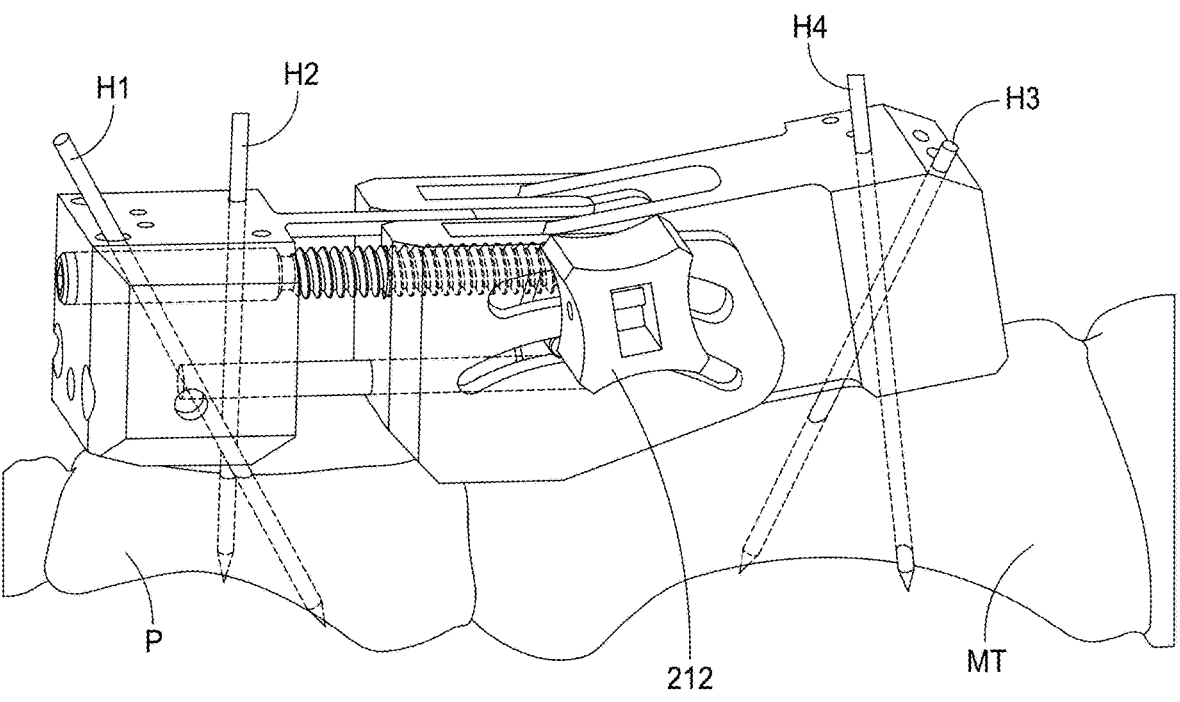
FIG. 18 and FIG. 19 are views showing two converging anchoring wires placed in each of the phalanx and the metatarsal.
Figure 19:
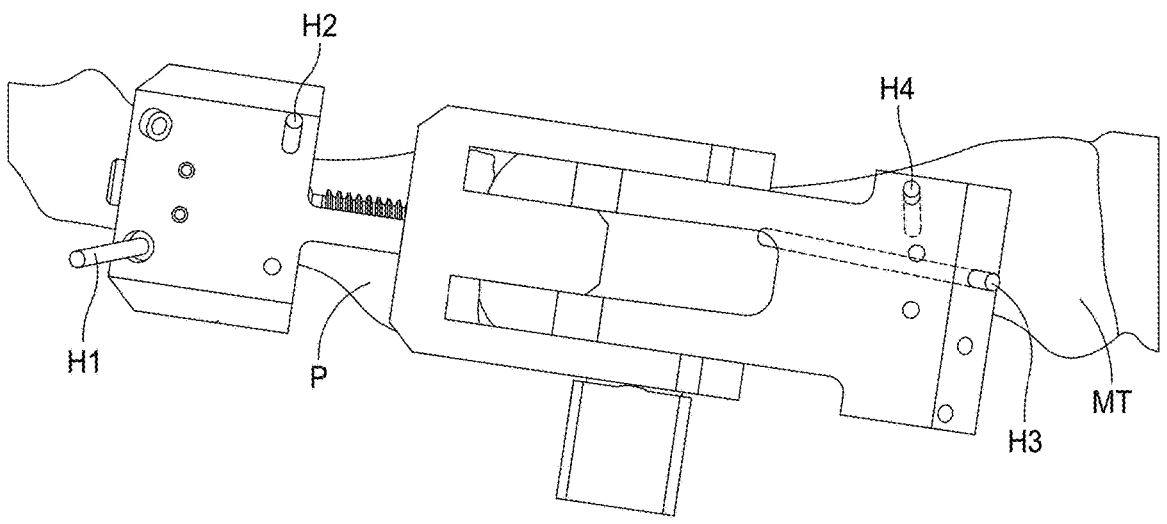

Two converging anchoring wires H1, H2 are then placed in the phalanx P and two converging anchoring wires H3, H4 in the metatarsal MT, as shown in FIG. 18. If there is any desirable hallux valgus present, a non-central option may be chosen for the anchoring wires H3 and H4 in the metatarsal MT. The top view of FIG. 19 shows an anatomic variant that would lead to placement of a non-central anchoring wire option into the metatarsal MT.

Figure 20:
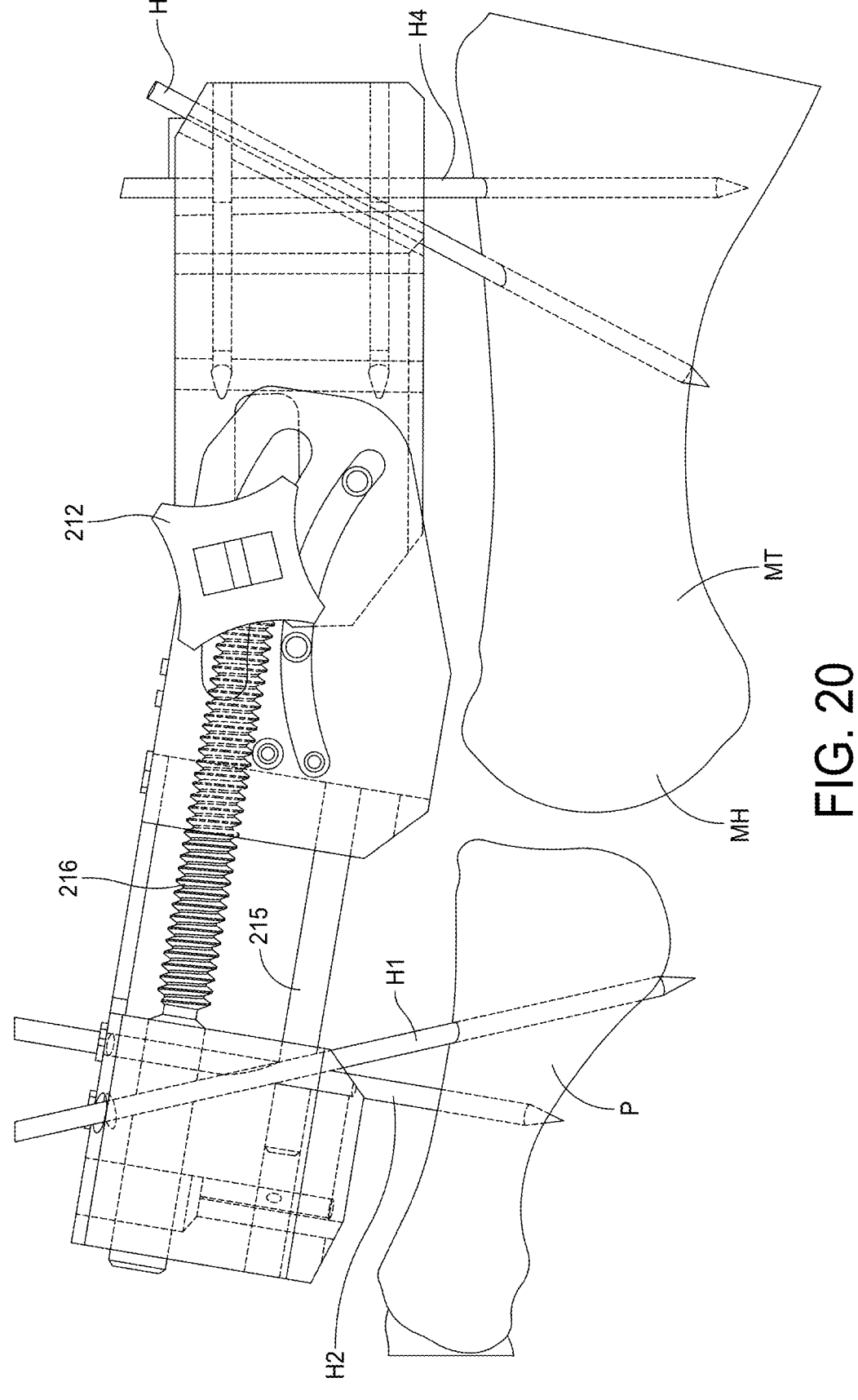
FIG. 20 shows the anchored phalanx distracted from the metatarsal.

Distraction is now possible, shown in FIG. 20, via the lead screw 216 and dowel 215 mechanism. The lead screw 216 can be rotated to separate the phalanx P from the metatarsal MT. This facilitates preparing the MTP joint for fusion (i.e., removal of cartilage and fenestration of subchondral cortical surface). As needed, the phalanx P can be plantarflexed or dorsiflexed to aid in MTP joint preparation as long as the knob 212 is loose. That is, the phalanx guide 214 and the connecting body 211 can rotate with respect to each other, effectively also rotating the phalanx P relative to the metatarsal MT in which the dorsal guide 210 is attached via the anchoring wires H1-H4. The pins-in-curved-slot design (i.e., the pins of the phalanx guide 214 fit into the curved slot of the connecting body 211) allows this dorsiflexion to occur about the estimated center of the metatarsal head MH.

Figure 21A:
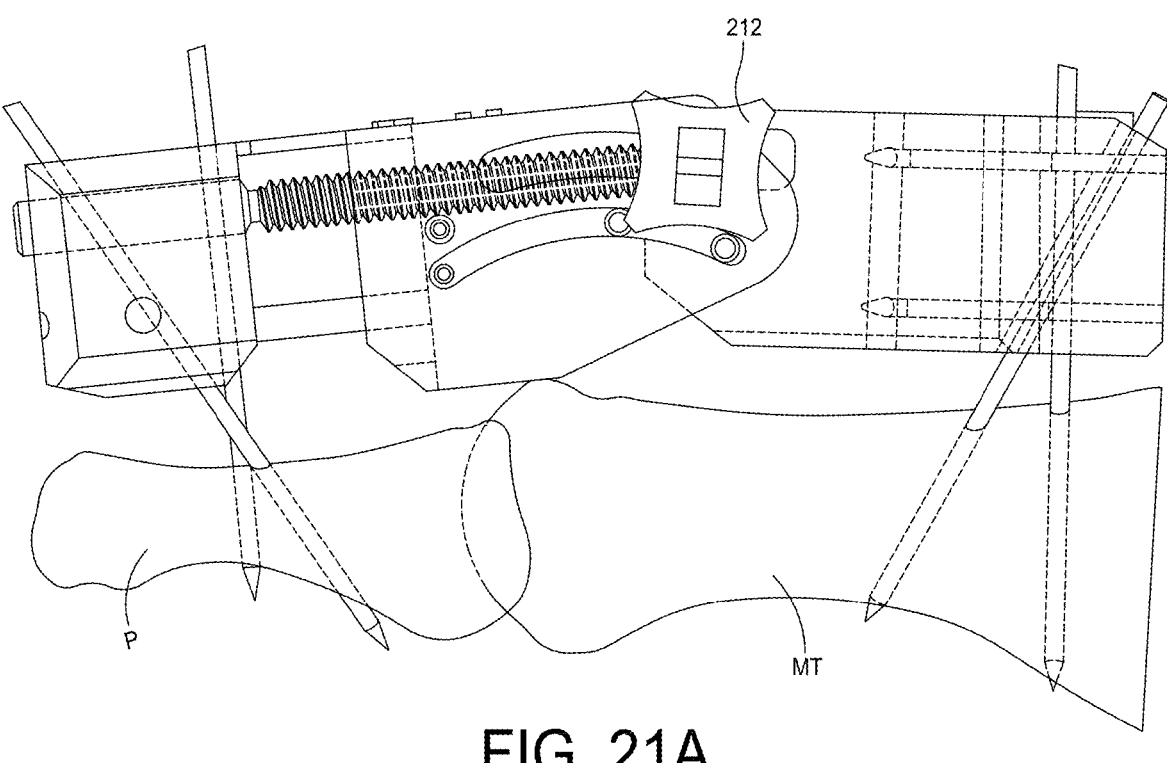
FIG. 21A and FIG. 21B show a return to neutral distraction and selection of desired dorsiflexion angle between metatarsal and phalanx.
Figure 21B:
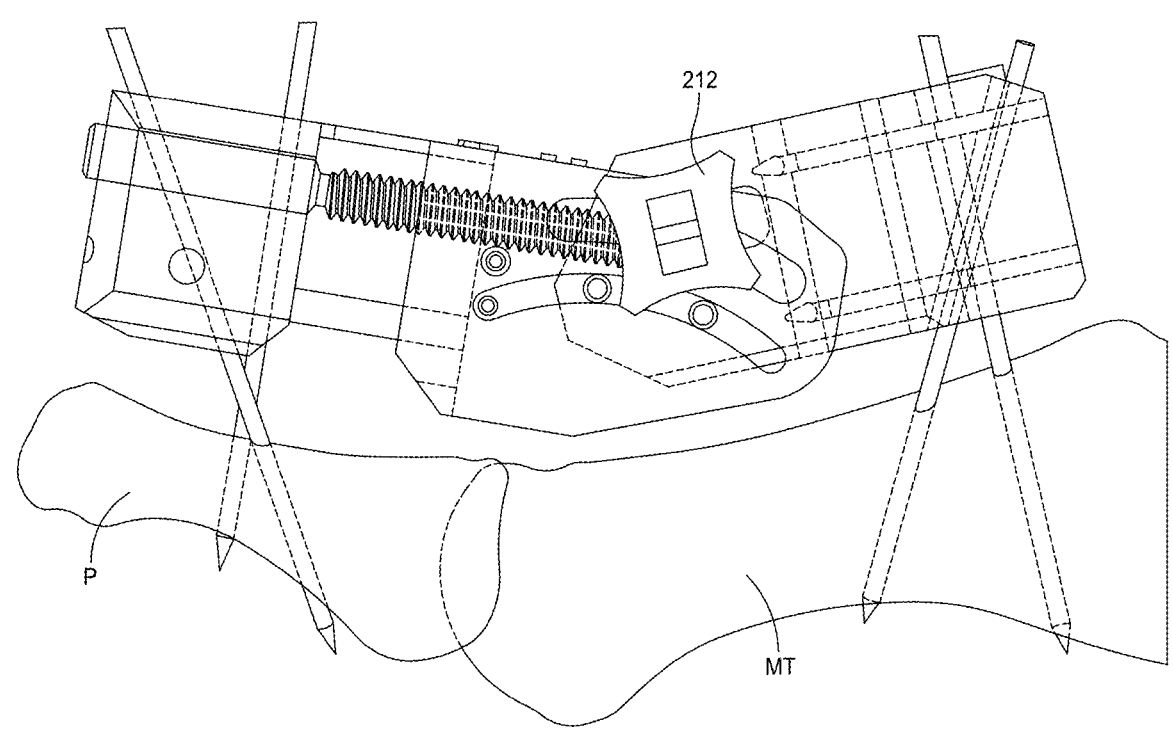
Figure 22:
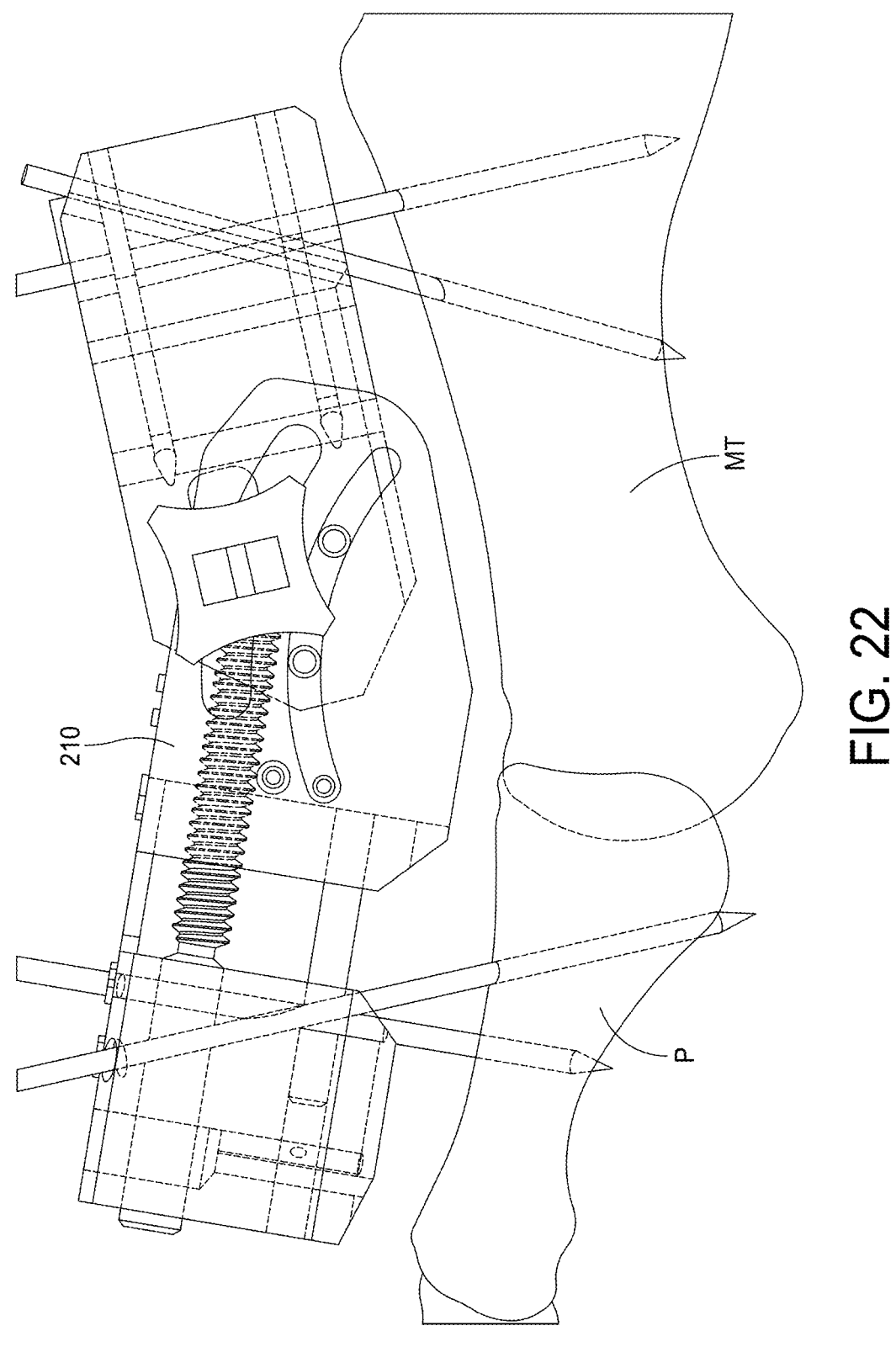
FIG. 22 shows MTP compression.

Once the MTP joint preparation is complete, distraction is returned to the starting level, as shown in FIG. 21A. The final selection of desired dorsiflexion can now be dialed in and locked via the knob 212, shown in FIG. 21B. Note that the position of the knob 212 can be moved to the other side of the dorsal guide 210 for use with a left foot. Optionally, the dorsal guide 210 can include two knobs 212, one on each side of the dorsal guide 210. As shown in FIG. 22, MTP compression can now be achieved by rotating the same lead screw 216 and dowel 215 mechanism. The dorsal guide 210 remains in place stabilizing the MTP joint correction for the remainder of the procedure.

Figure 23:
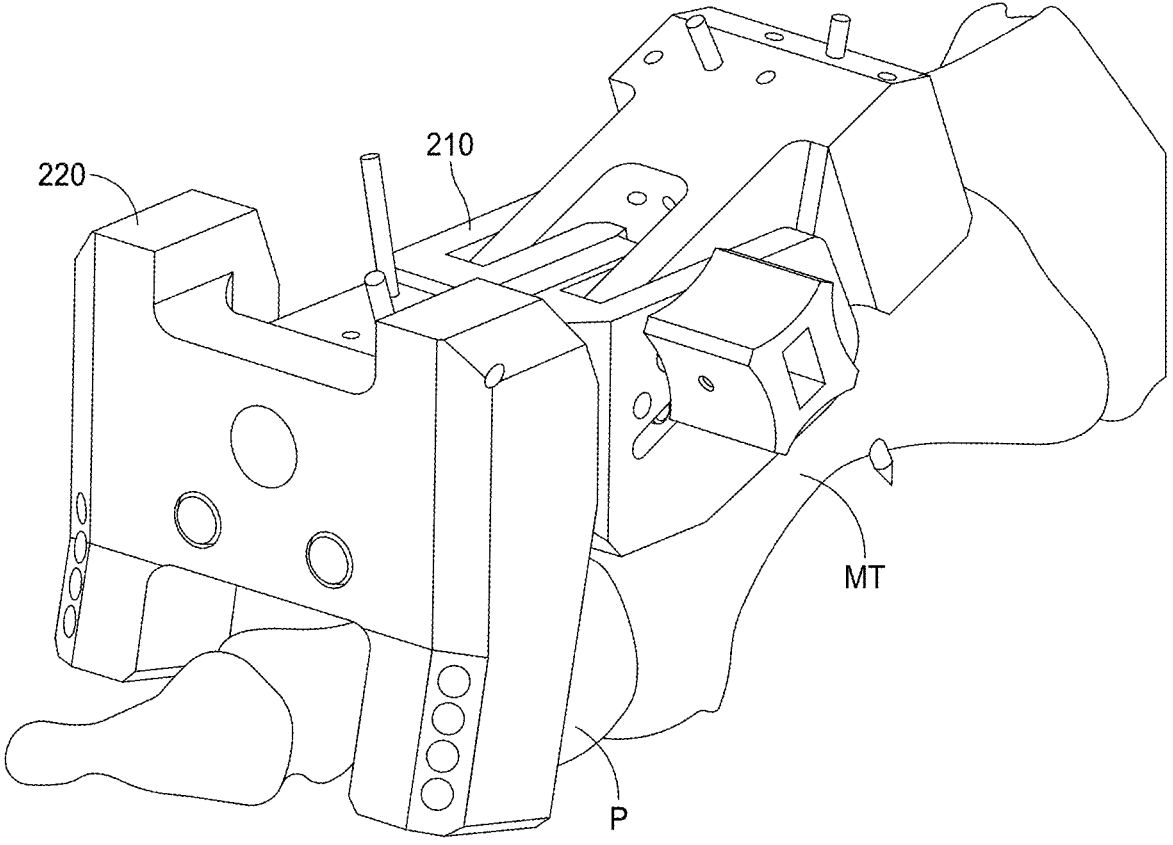
FIG. 23 show an outrigger inserted into a dorsal guide.
Figure 24:
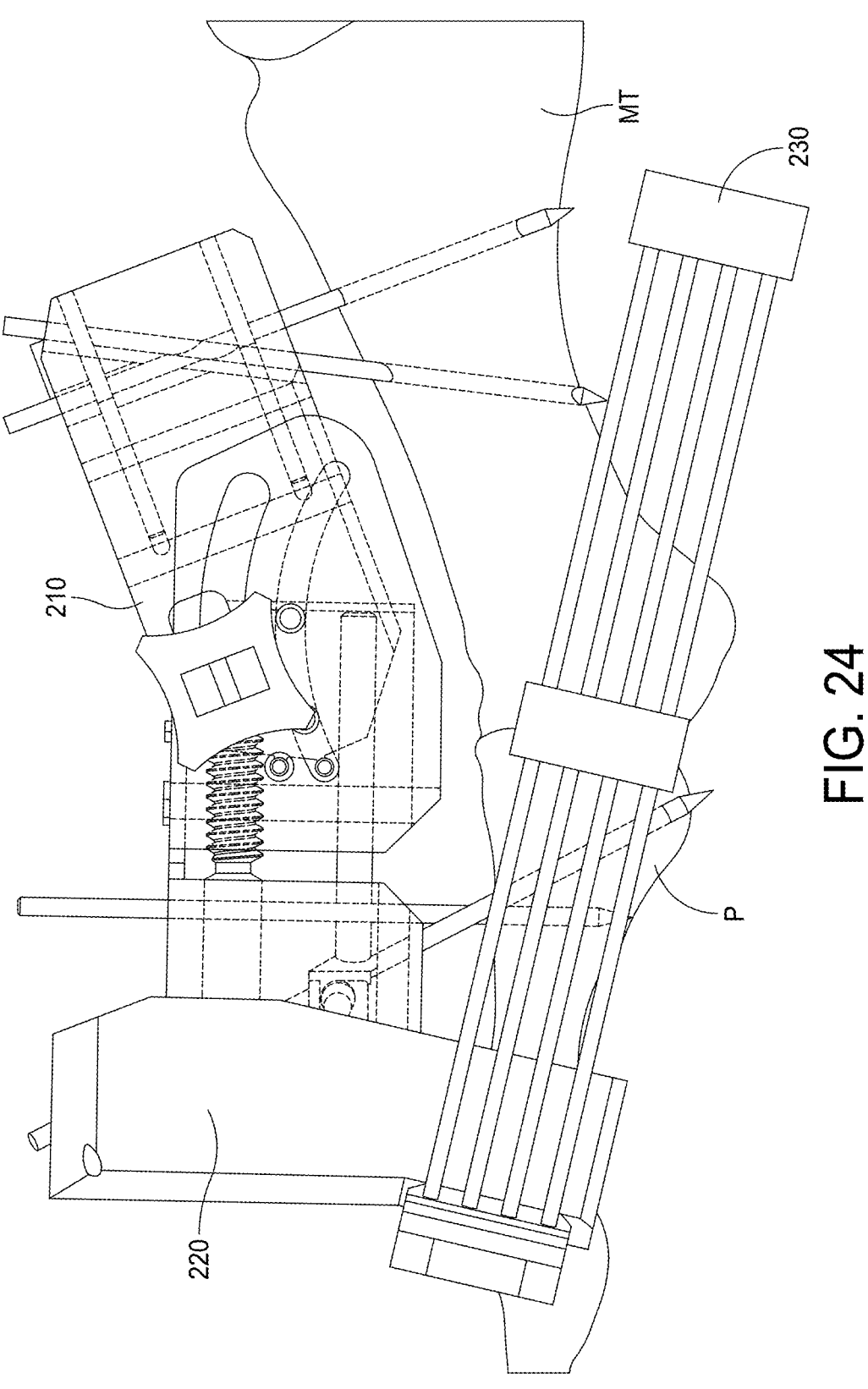
FIG. 24 shows a pronged trajectory guide in place over a MTP joint.

Once the MTP joint is oriented, as shown in FIG. 23, the outrigger 220 is assembled to the dorsal guide 210 and the pronged trajectory guide 230 is then inserted into the corresponding holes of the outrigger 220, as shown in FIG. 24. The outrigger 220 can be attached to the dorsal guide 210 using a set of dowel pins 250 each with a perpendicular spring plunger that fit into associated holes in the phalanx guide 213 body. The dowel pins 250 can be more clearly viewed in FIG. 25. This combination is used to select between the trajectory options for the distal-medial-to-proximal-lateral fastener indicated by the extending prongs of the pronged trajectory guide 230. The pronged trajectory guide 230 includes parallax ROI such that when the x-ray plane and the pronged trajectory guide 230 are aligned properly (true lateral to the distal end of the pronged trajectory guide 230), the overhanging prongs of the pronged trajectory guide 230 show exactly where the trajectories project in the bones. These parallax ROIs are embedded in the section of the pronged trajectory guide 230 that inserts into outrigger 220. The plantar-most viable trajectory is selected.

Figure 25:
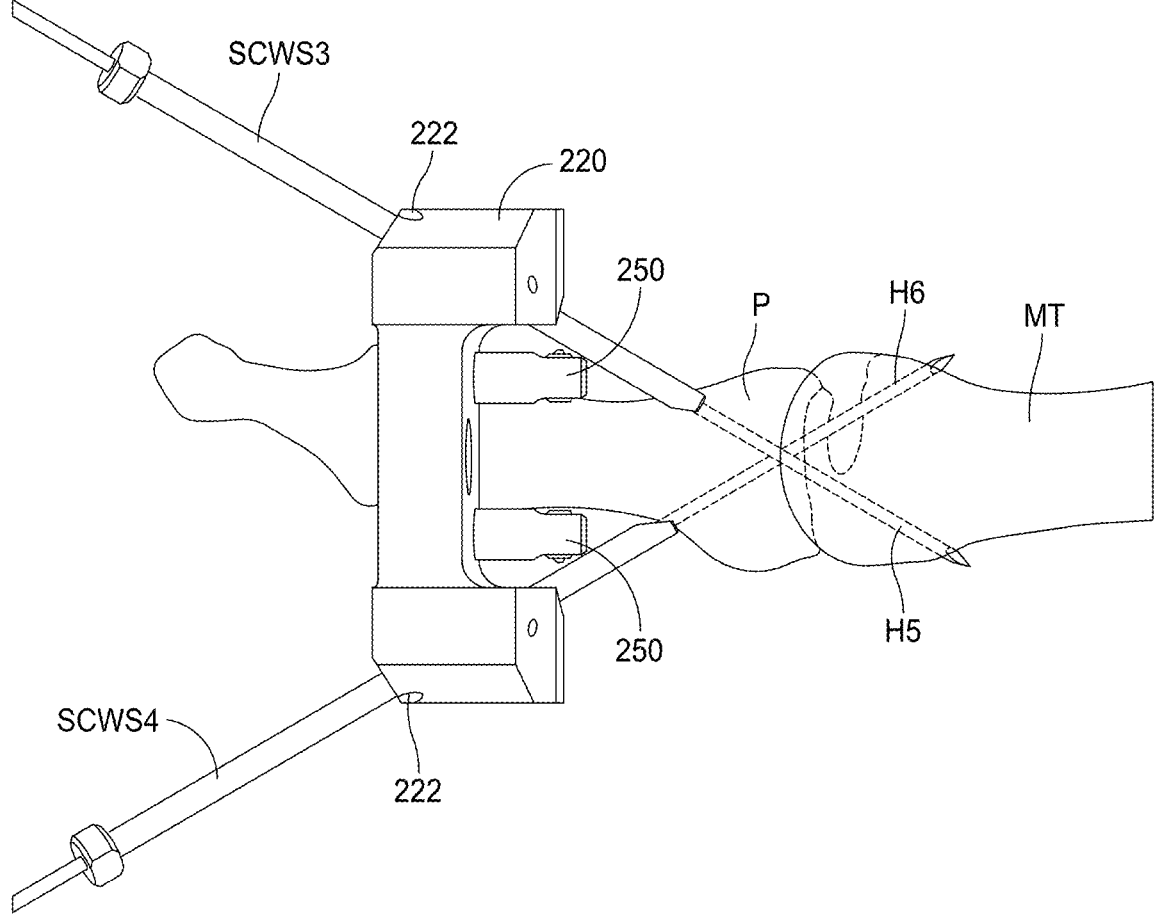
FIG. 25 shows single-chamfer wire sleeves and corresponding guide wires in place.

In other embodiments, the outrigger 220 can be assembled to the dorsal guide 210 using alternative mechanisms such as a screw, a dovetail, a simple pin cluster in a hole cluster or from a different direction (i.e., dorsal, medial, etc.). The outrigger 220 can have an adjustable height with a vertical screw and dowel mechanism in place of the discreet hole options. In such a case, the pronged trajectory guide 230 could then only have a single prong. The outrigger 220 can have an adjustable angle instead of a static angle as shown in FIG. 25. This angle could be locked with a locking set screw or by another mechanism, and both sides of the outrigger 220 could be independently adjustable.

Additionally, additional holes 222 in the outrigger 220 are sized and located such that a guide wire can be placed through the holes (likely one at a time) (see OH1 and OH2 in FIG. 12) while a chamfered wire sleeve is placed against the skin, as shown in FIG. 25. The overlapping of these indicators on the anterior-posterior X-ray would indicate the planned anterior-posterior trajectory of the guide wire and implant fastener. This would be more useful if the outrigger 220 had an adjustable angle in the anterior-posterior view.

Once a trajectory is selected, a small incision is made in a projected location on the toe, a single-chamfer wire sleeve is inserted down to bone, and a fastener guide wire is placed through the single-chamfer wire sleeve and into the bones. Selecting a second trajectory indication is not necessary because the analogous hole is provided for the proximal-medial-to-distal-lateral fastener on the other side of the outrigger 220 and is designed to be spaced appropriately with the first trajectory. FIG. 25 shows trajectories provided by the outrigger 220 in an anterior-posterior view. The dorsal guide 210 and the pronged trajectory guide 230 are omitted from FIG. 25 for clarity. FIG. 25 shows the trajectories of single-chamfer wire sleeves SCWS3 and SCWS4 that have been placed through the outrigger 220 and corresponding fastener guide wires H5 and H6 through the single-chamfer wire sleeves and into the phalanx P and the metatarsal MT bones.

Figures 26A, 26B:
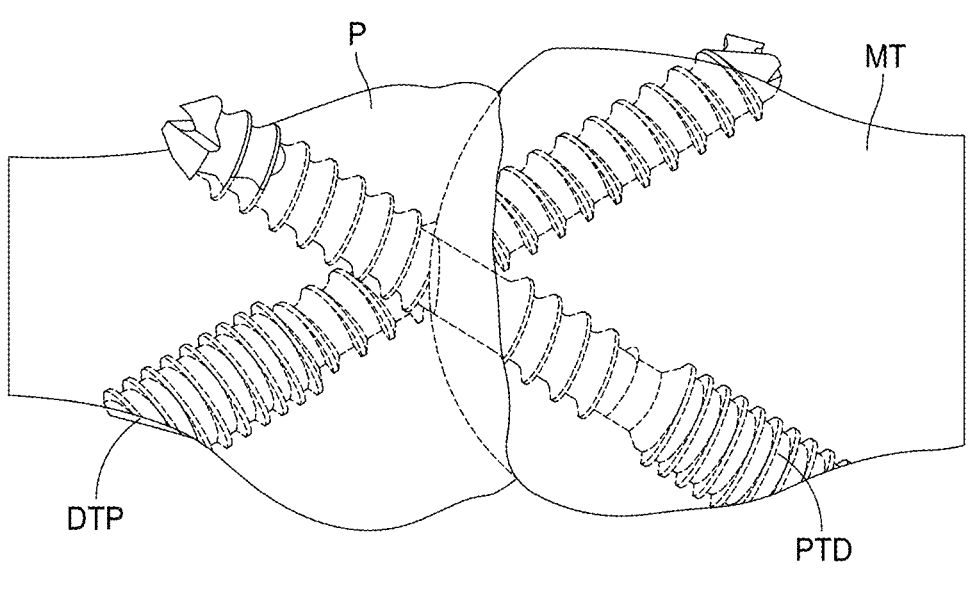
FIG. 26A and FIG. 26B show the result of a MTP fusion procedure.

With the guide wires H5 and H6 placed, the single-chamfer wire sleeves SCWS3 and SCWS4 and the outrigger 220 can be removed. Depth gauging, pre-drilling, and driving the fasteners DTP or PTD implants follow. Once the DTP and PTD fasteners are in place, the dorsal guide 210 and the outrigger 220 are then removed. FIGS. 26A and 26B show the result of the MTP fusion procedure. FIG. 26A is an anterior-posterior (top) view and FIG. 26B is a lateral (side) view of the MTP joint showing the DTP and PTD fasteners in place.

Figure 28:
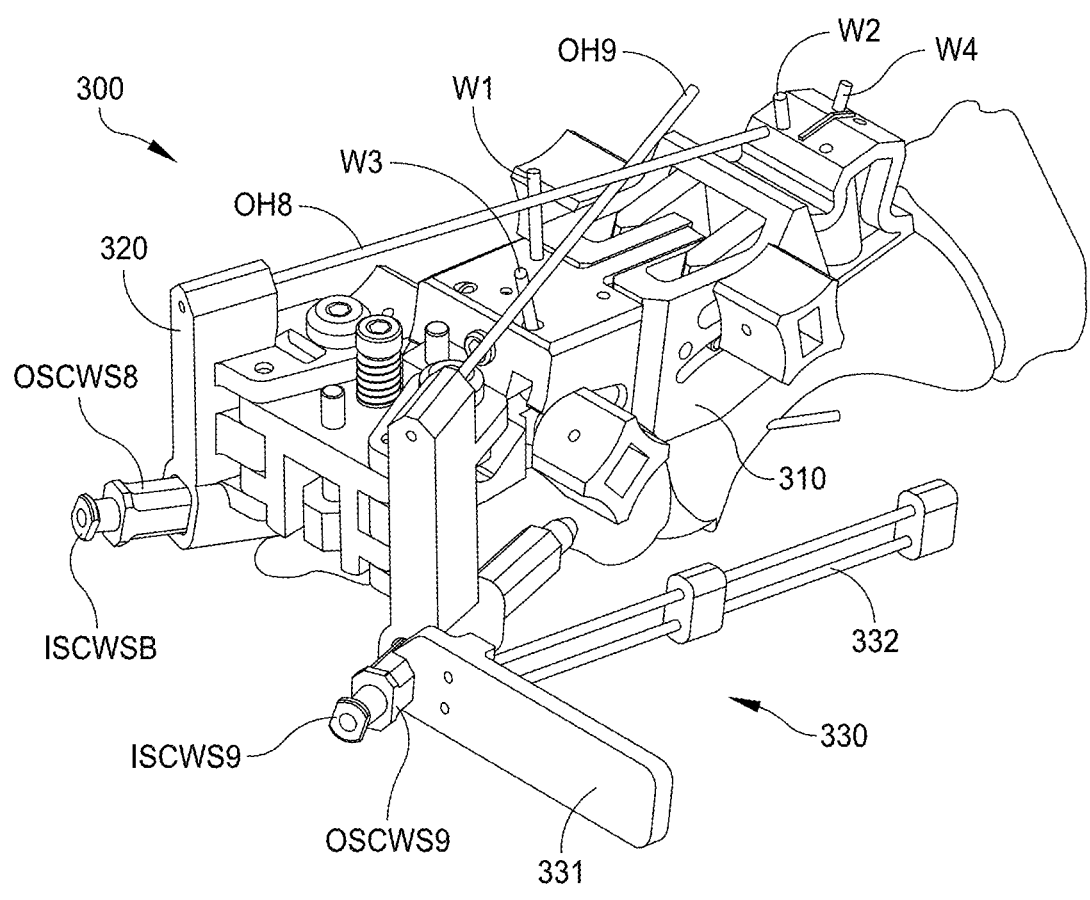
FIG. 28 shows a system for MTP joint fusion according to another embodiment of the present disclosure.

A fastener outrigger system 300 for metatarsal phalangeal (MTP) joint fusion according to a third embodiment of the present disclosure is shown in FIG. 28. The system 300 is used to align (i) anchoring wires to be placed into the metatarsal and phalanx bones forming the MTP joint for stabilization, (ii) the metatarsal and phalanx bones for fusion, and (iii) fixation fasteners. The system 300 also includes features in which medial-lateral angulation, dorsal-plantar angulation, and dorsal-plantar elevation of trajectory guides can be adjusted during surgery to aid fixation fastener placement. The fastener outrigger system 300 can include a dorsal guide 310, an outrigger assembly 320, a pronged trajectory guide 330 that can include an upright portion 331 and an indicator portion 332, overhanging wires OH8, OH9, outer single-chamfer wire sleeves OSCWS8, OSCWS9, inner single-chamfer wire sleeves ISCWS8, ISCWS9, and anchoring wires W1 to W4. It is noted that although FIG. 28 shows all of the components of the fastener outrigger system 300, some of the components may not be selected or used by a surgeon at the same time or at all during a procedure.

Figure 29:
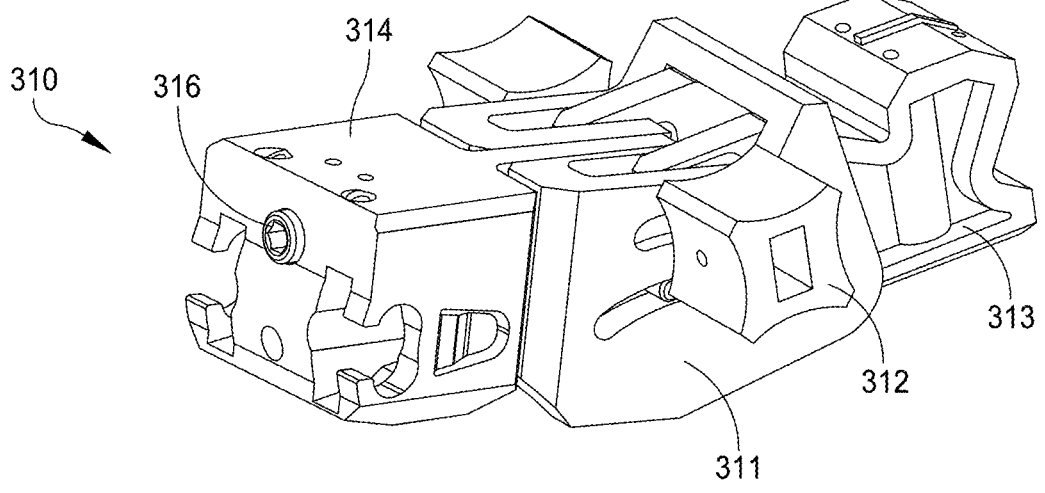
FIG. 29 shows portions of a dorsal guide.

FIG. 29 shows portions of the dorsal guide 310 and their relative orientations to each other. As shown, the dorsal guide 310 can include a connecting body 311, a first knob 312, a metatarsal guide 313, a phalanx guide 314, and a lead screw 316. The connecting body 311, the first knob 312, the metatarsal guide 313, the phalanx guide 314, the second knob 318, the adjustment block 317, and the arm anchor 321 can be made of a plastic or polymer and can include radiopaque indicators (ROI) on or within these components.

Figure 30:
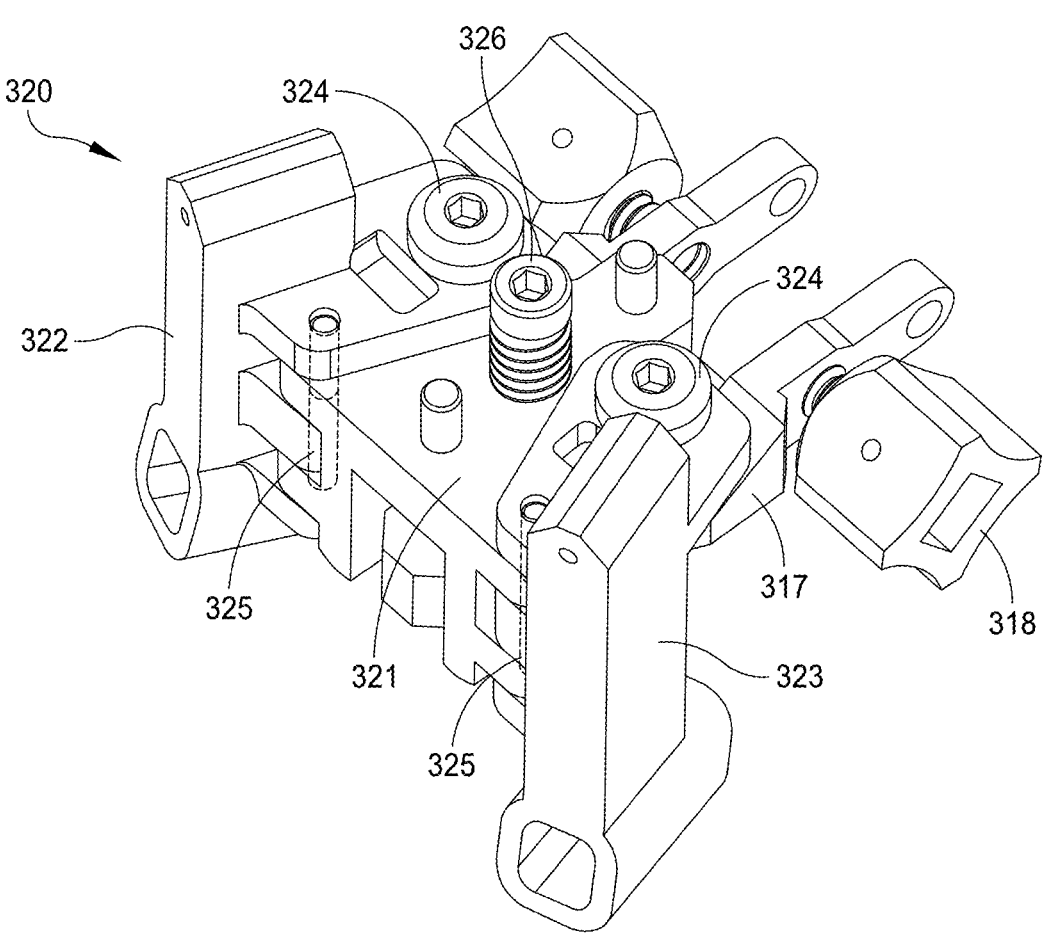
FIG. 30 shows portions of an outrigger assembly.

FIG. 30 shows portions of the outrigger assembly 320 that can include two outrigger arms 322 and 323 that are attached to the arm anchor 321 via corresponding screws 324 and pins 325. As shown, the outrigger arms 322, 323 can include through holes at one (top) end to accept the overhanging wires OH8 and OH9 and through holes at the other (bottom) end to accept the outer single-chamfer wire sleeves OSCWS8 and OSCWS9. The outrigger assembly 320 can be moved relative to the adjustment block 317 via rotation of an adjustment screw 326 as discussed below. Further details of the individual components are included in the operation description below.

The system 300 has multiple features that allow it to aid in performing the entire MTP fusion procedure. After an incision is made, at the MTP joint and the MTP joint is released from a medial approach, the dorsal guide 310 is then placed over the first metatarsal MT and phalanx P, as shown in the side view of FIG. 31. ROIs can be used to align the distal end with the phalanx central axis, the distal-proximal position with the MTP joint space, and the proximal end with the metatarsal central axis. Manual reduction of any present hallux valgus is possible in this step. Each set of ROIs is "doubled" to provide a parallax indicator to ensure the x-ray viewing plane is aligned with the dorsal guide 310 and providing accurate information.

Figure 31:
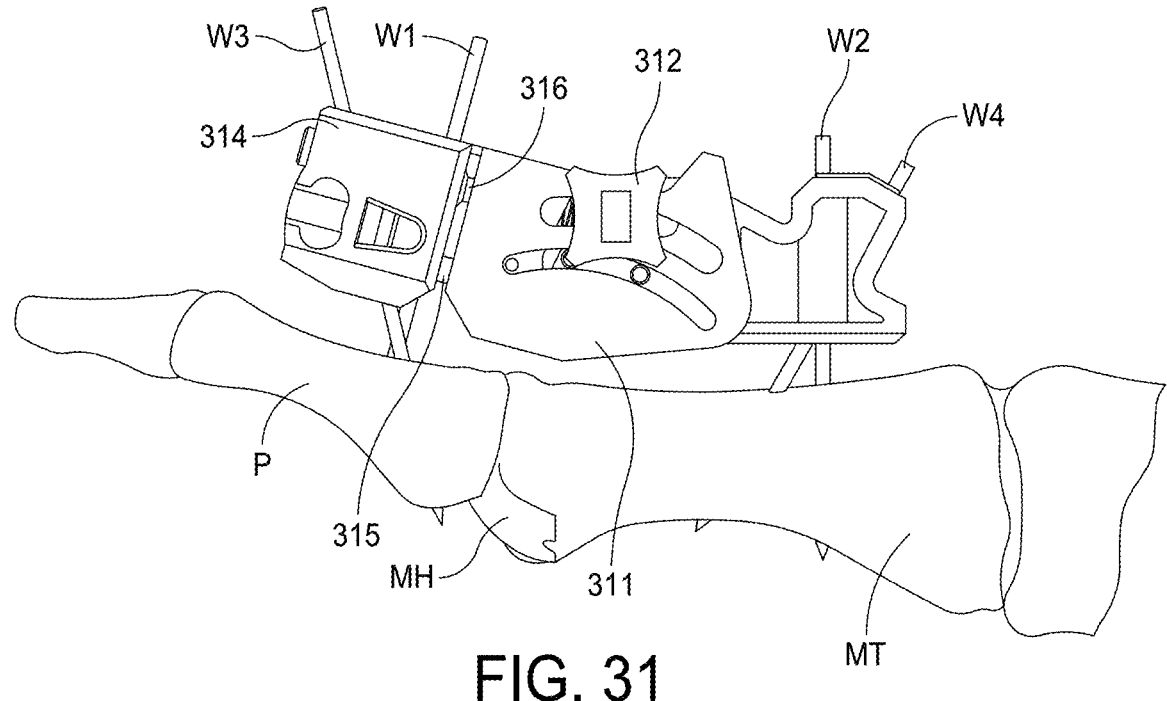
FIG. 31 shows two converging anchoring wires placed in each of the phalanx and the metatarsal.

Two converging anchoring wires W1, W3 are then placed in the phalanx P and two converging anchoring wires W2, W4 in the metatarsal MT, as shown in FIG. 31. As previously described, distraction is now possible (not shown) via a lead screw 316 and dowel 315 mechanism. The lead screw 316 can be rotated to separate the phalanx P from the metatarsal MT. This facilitates preparing the MTP joint for fusion (i.e., removal of cartilage and fenestration of subchondral cortical surface). As needed, the phalanx P can be plantarflexed or dorsiflexed to aid in MTP joint preparation as long as the knob 312 is loose. That is, the metatarsal guide 313 and the connecting body 311 can rotate with respect to each other, effectively also rotating the phalanx P relative to the metatarsal MT in which the dorsal guide 310 is attached via the anchoring wires W1-W4. The pins-in-curved-slot design (i.e., the pins of the metatarsal guide 313 fit into the curved slot of the connecting body 311) allows this dorsiflexion to occur about the estimated center of the metatarsal head MH.

Once the MTP joint preparation is complete, distraction is returned to the starting level. The final selection of desired dorsiflexion can now be dialed in and locked via the knob 312. Note that the position of the knob 312 can be moved to the other side of the dorsal guide 310 for use with a left foot. Optionally, the dorsal guide 310 can include two knobs 312, one on each side of the dorsal guide 310, as shown in FIGS. 28 and 29. MTP compression can now be achieved by rotating the same lead screw 316 and dowel 315 mechanism. The dorsal guide 310 remains in place to stabilize the MTP joint correction during the remainder of the procedure.

The outrigger assembly 320 can be attached to the phalanx guide 314. For medial-lateral angulation adjustment before incisions, the overhead wires OH8/OH9, the outer single-chamfer wire sleeve OSCWS8/OSCWS9, and the inner single-chamfer wire sleeves ISCWS8/ISCWS9 can be used with the outrigger assembly 320. One of the overhead wires OH8/OH9 can be placed through a corresponding hole in the outrigger assembly 320. A corresponding outer single-chamfer wire sleeve OSCWS8/OSCWS9 can be partially inserted, and a corresponding inner single-chamfer wire sleeves ISCWS8/ISCWS9 can be mostly inserted. Then, while aligning the centers of overhead wire and inner single-chamfer wire sleeve using real-time X-ray imaging, the medial-lateral angulation can be chosen and locked in with set screws 324. Then these steps can be repeated on the other side.

Figure 32:
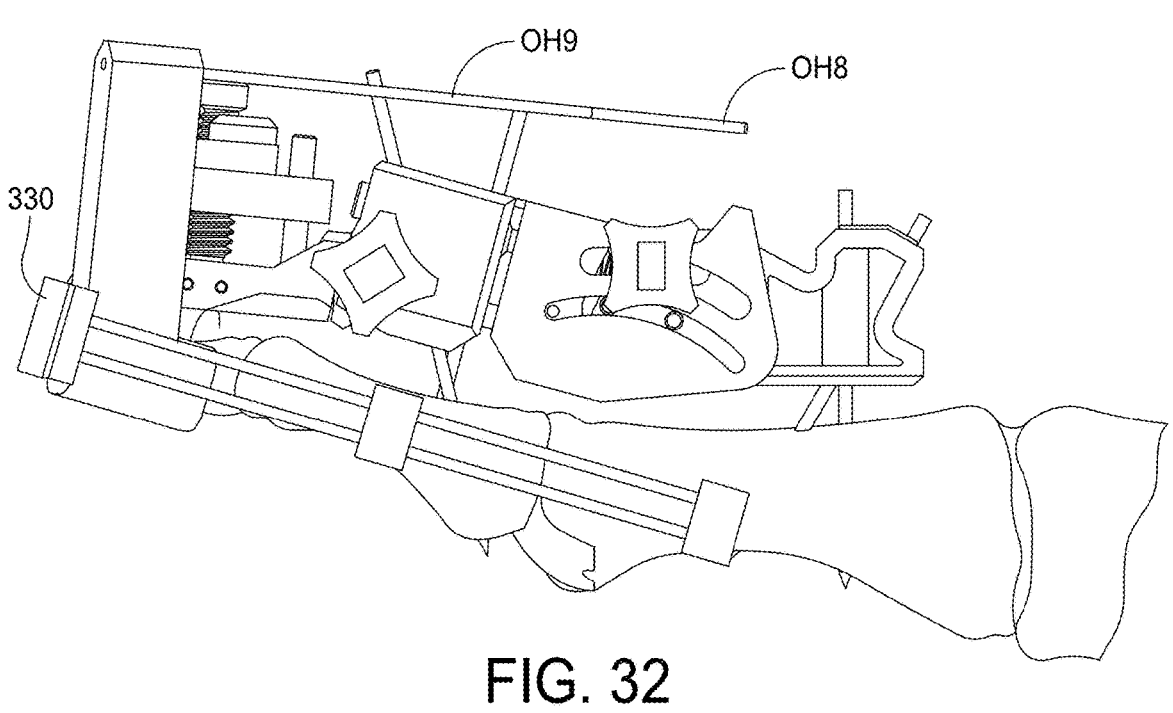
FIG. 32 and FIG. 33 show a pronged trajectory guide in place over a MTP joint.
Figure 33:
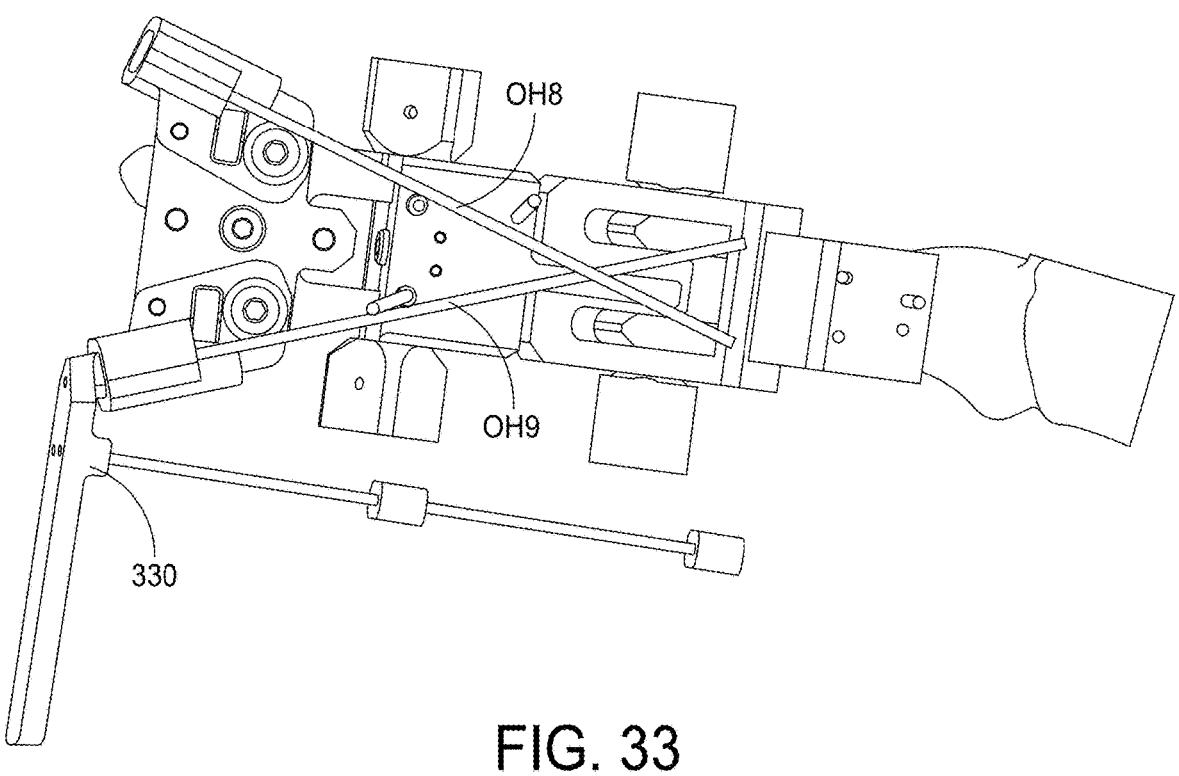

The pronged trajectory guide 330 can then be inserted into the corresponding holes of the outrigger assembly 320, as shown in side view of FIG. 32 and top view of FIG. 33. The pronged trajectory guide 330 includes parallax ROIs, like those previously described, such that when the x-ray plane and the pronged trajectory guide 330 are aligned properly (true lateral to the distal end of the pronged trajectory guide 330), the overhanging prongs of the pronged trajectory guide 330 show exactly where the fixation fastener trajectories project in the bones.

Figure 34:
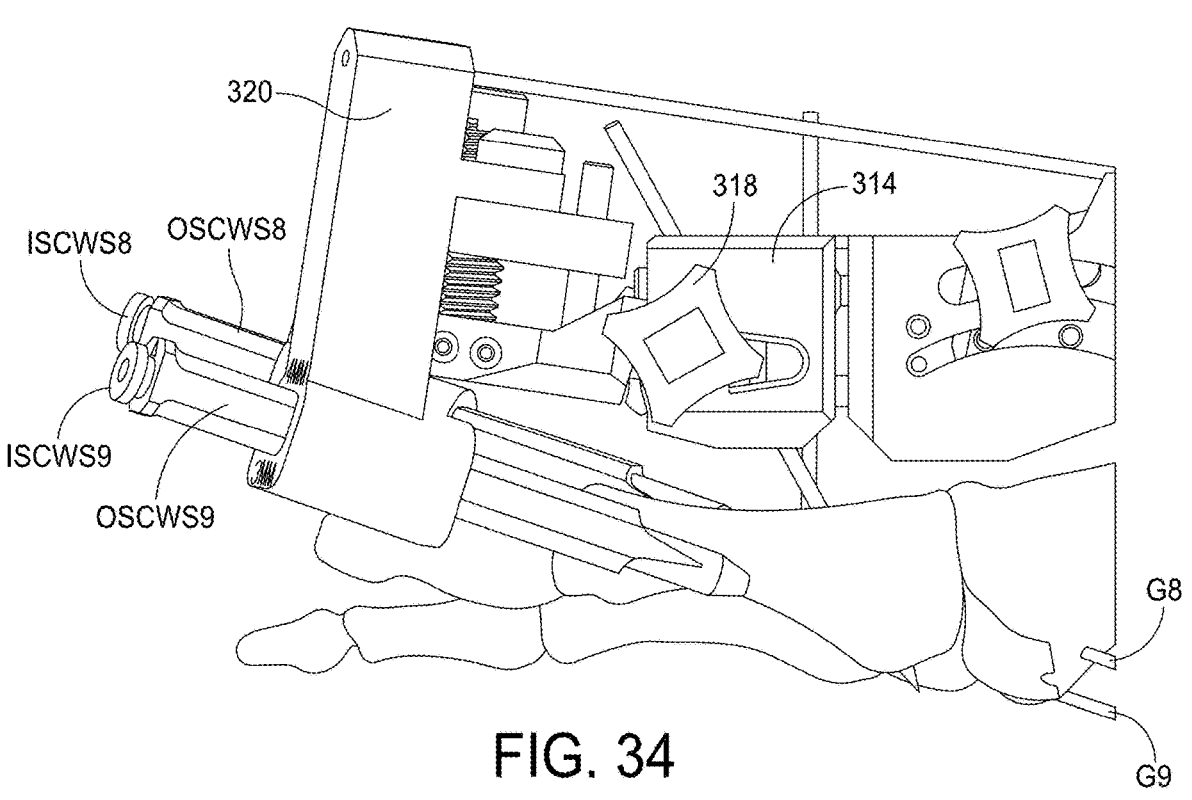
FIG. 34 and FIG. 35 show how an angle of an outrigger assembly can be changed.
Figure 35:
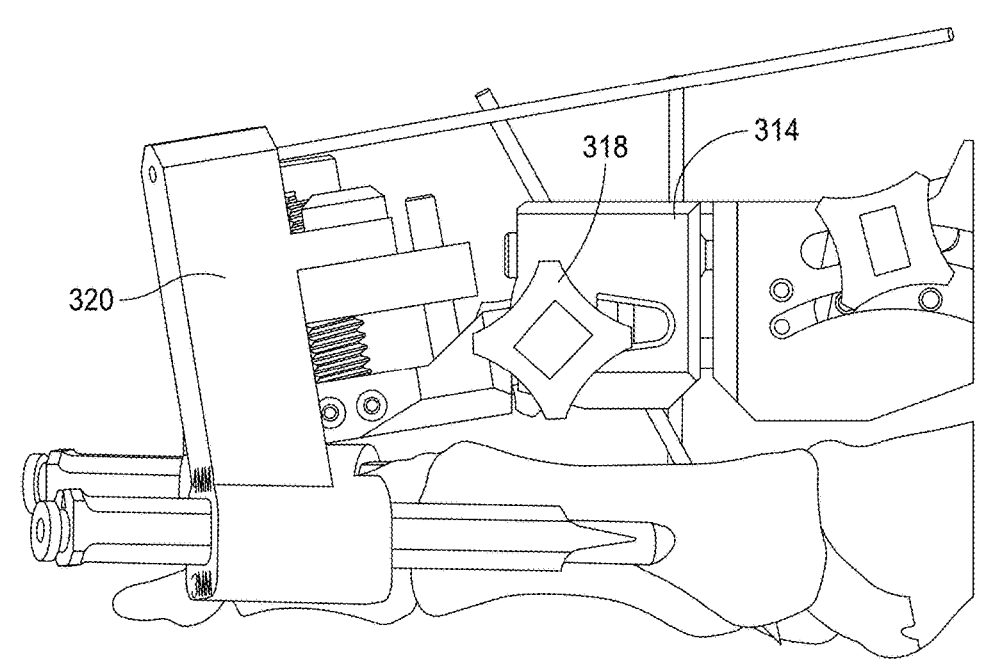
Figure 36:
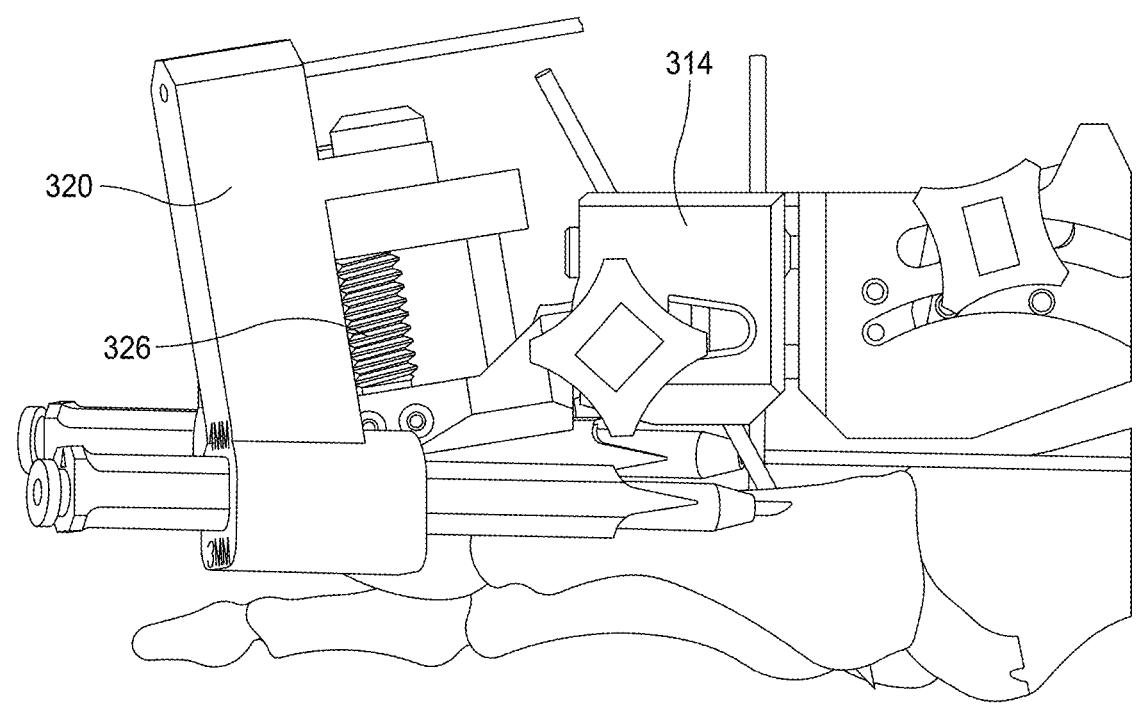
FIG. 36 and FIG. 37 show how an elevation of an outrigger assembly can be changed.
Figure 37:
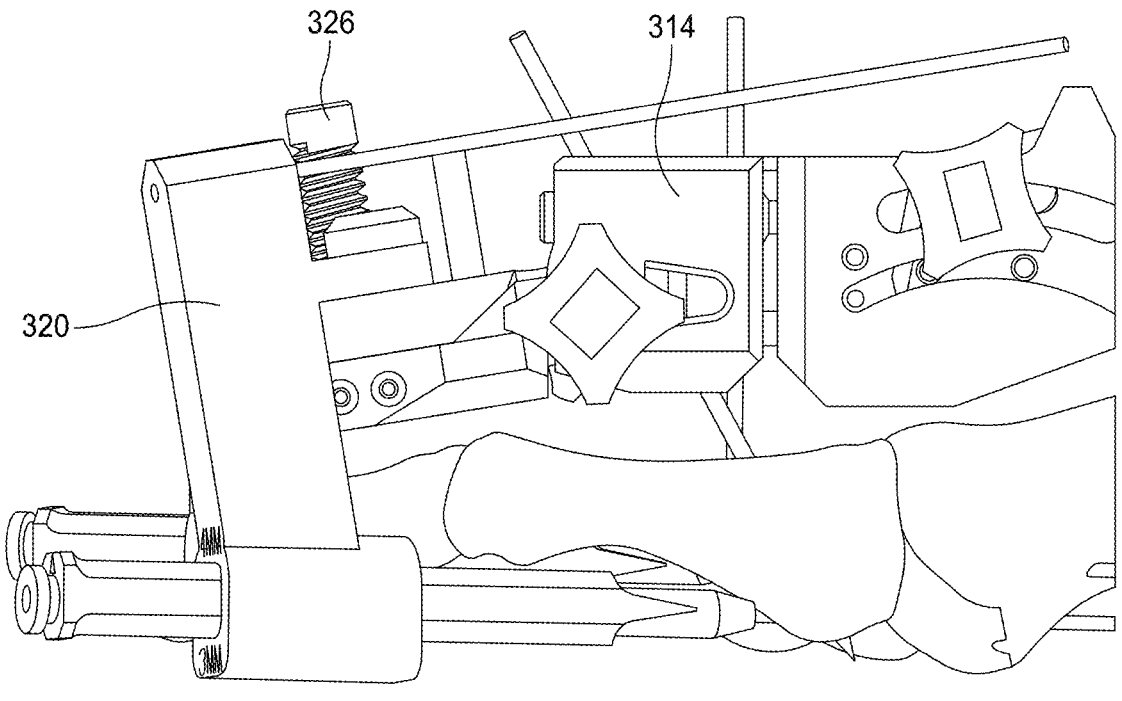

Further adjustment of the fastener outrigger system 300 is possible by moving the outrigger assembly 320, as shown in FIGS. 34 and 35. In FIGS. 34 and 35, the pronged trajectory guide 330 has been replaced by the outer single-chamfer wire sleeves OSCWS8 and OSCWS9, the inner single-chamfer wire sleeves ISCWS8, ISCWS9, and corresponding guide wires to show how the fixation fastener trajectories can be adjusted. For example, FIGS. 34 and 35 show that the angle of the outrigger assembly 320 with respect to the dorsal guide 310 can be changed by loosening the knob 318 and rotating the outrigger assembly 320 about the phalanx guide 314. FIG. 35 shows that the outrigger assembly 320 has been rotated in a counter clockwise direction as compared to its position in FIG. 34. The second knob 318 can be tightened to lock the angle of the outrigger assembly 320. In another example, FIGS. 36 and 37 show that an elevation of the outrigger assembly 320 can be raised and lowered with respect to the phalanx guide 314 via the adjustment screw 326. FIG. 37 shows the outrigger assembly 320 has been lowered with respect to the position shown in FIG. 36. Thus, the adjustment mechanisms in the fastener outrigger system 300 provide the surgeon a great degree of intraoperative freedom in orienting trajectory guides for fixation fastener placements with the pronged trajectory guide 330 indicating the precise path the fasteners will be implanted.

Figure 38:
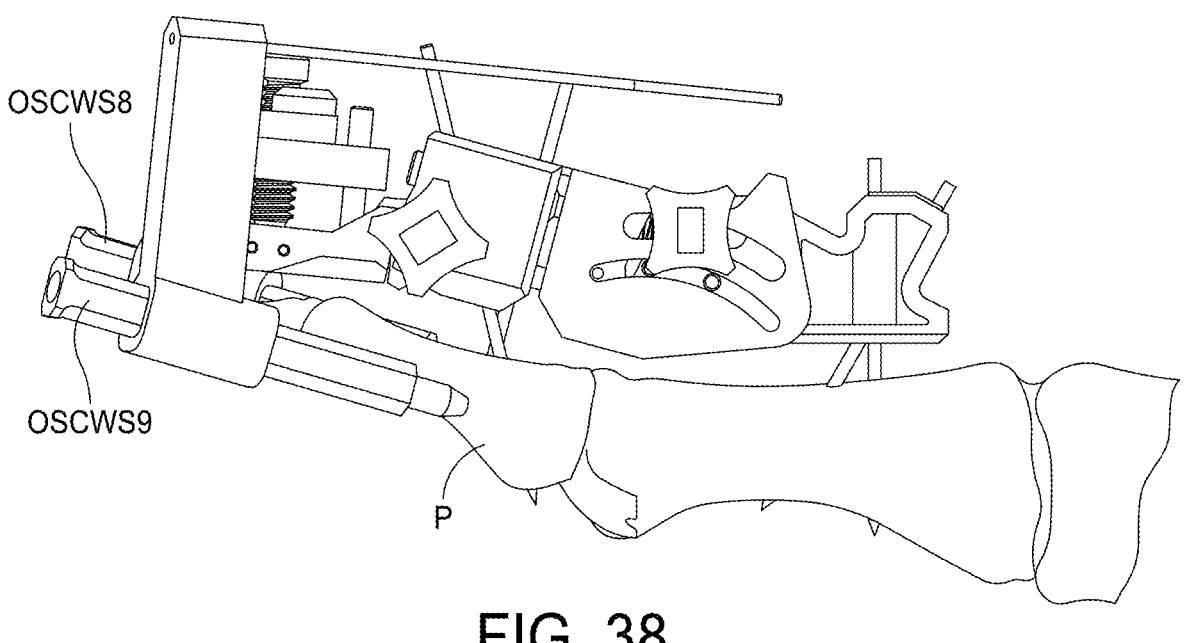
FIG. 38 shows outer single-chamfer wire sleeves in place.
Figure 39:
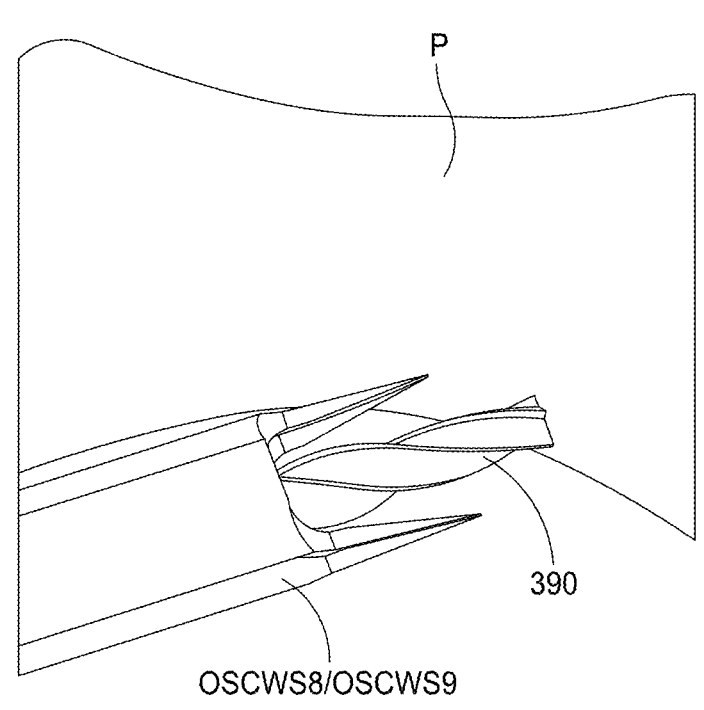
FIG. 39 shows a burr used to notch a bone.

After the outrigger assembly 320 has been positioned to select a desired fixation fastener trajectory, the pronged trajectory guide 330 can be removed and the outer single-chamfer wire sleeves OSCWS8 and OSCWS9 can be inserted through corresponding holes in the outrigger assembly 320, as shown in FIG. 38. Small incisions can be made in projected locations on the toe. As shown in FIGS. 36-39, the outer single-chamfer wire sleeves OSCWS8 and OSCWS9 can include at least one spike feature that can be used to temporarily anchor the outer single-chamfer wire sleeves OSCWS8 and OSCWS9 into bone while the sleeves are used for guiding. With the outer single-chamfer wire sleeves OSCWS8 and OSCWS9 in place, a cutting tool or burr 390 can be inserted through the outer single-chamfer wire sleeves OSCWS8 and OSCWS9 and used to notch or flatten portions of the phalanx P bone at the entry point, as shown in FIG. 39.

The diameter of the burr 390 can be sized to match the fixation fasteners. For example, the fastener system can be MICA™ Screws that are cannulated self-tapping headless compression fully threaded titanium alloy screws in various diameters and lengths. Alternatively, the burr 390 can include a smaller diameter tip for one fixation fastener diameter and a larger diameter mid-portion for a larger diameter fixation fastener.

Figure 40:
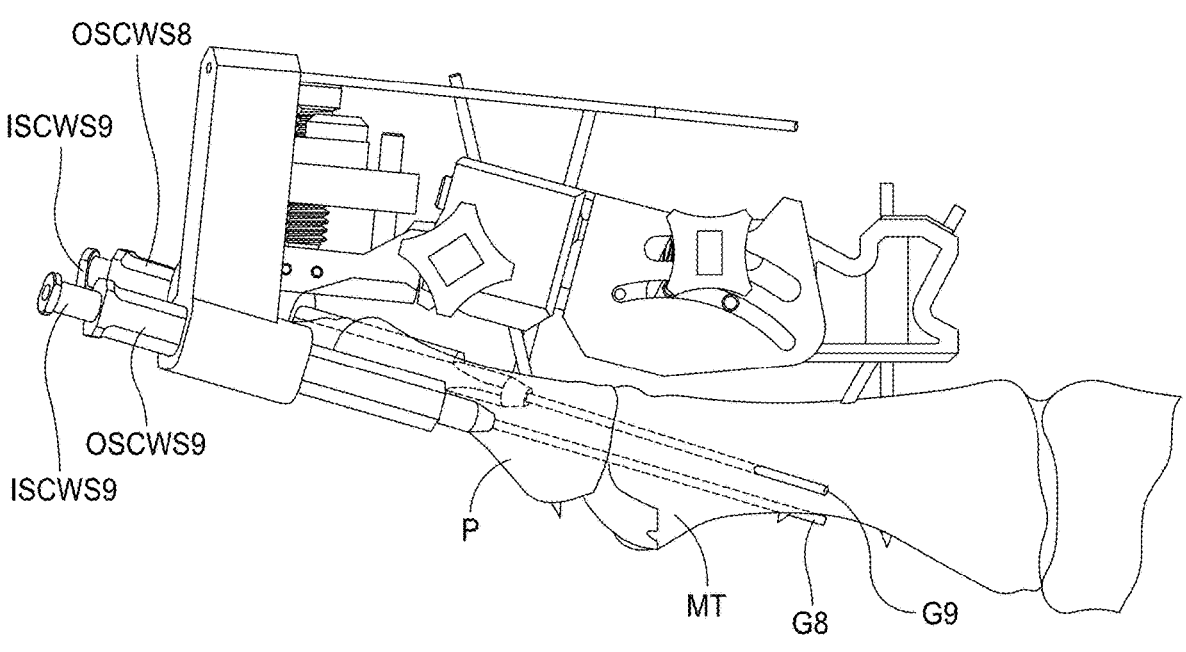
FIG. 40 shows inner single-chamfer wire sleeves and corresponding guide wires in place.

After the phalanx P has been notched, the inner single-chamfer wire sleeves ISCWS8, ISCWS9, can be inserted through the outer single-chamfer wire sleeves OSCWS8, OSCWS9 and used as guides to insert corresponding fastener guide wires G8, G9 through the inner single-chamfer wire sleeves ISCWS8, ISCWS9 and into the bones along the trajectory for the fixation fasteners, as shown in FIG. 40.

Figure 41:
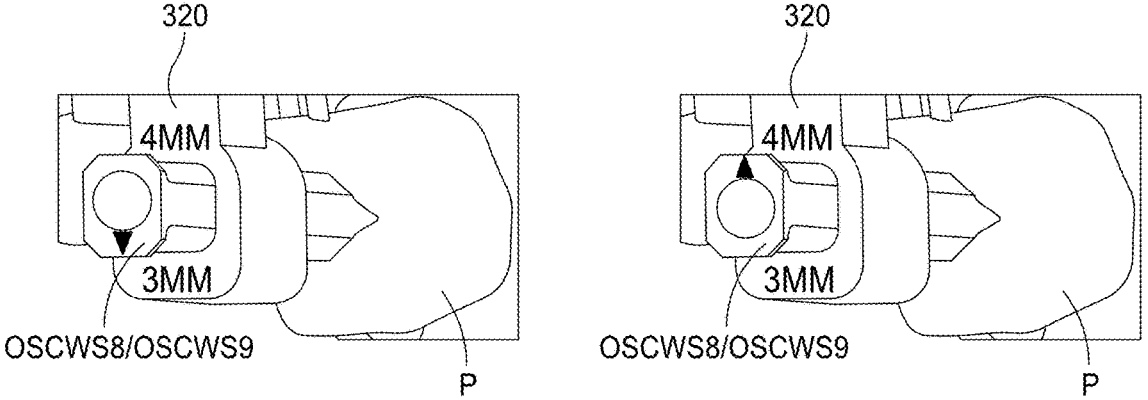
FIG. 41 shows an option for selecting a fixation fastener diameter.

In an embodiment, the outrigger assembly 320 and outer/inner wire sleeve system can be provided with a way that the surgeon can select and be guided for a certain fixation fastener diameter. FIG. 41 shows that there can be an option, for example, to select a 3 mm or a 4 mm diameter fastener. As shown, the bore through the outer single-chamfer wire sleeves OSCWS8, OSCWS9 can be offset such when placed though the outrigger assembly 320 the fastener guide wires G8, G9 can be closer together for 3 mm fasteners. Trajectories for both fastener diameters are accurately indicated by the pronged trajectory guide 330 that can directly show the 4 mm construct with the 3 mm construct at the "inner boundary" of the prongs.

Figure 42:
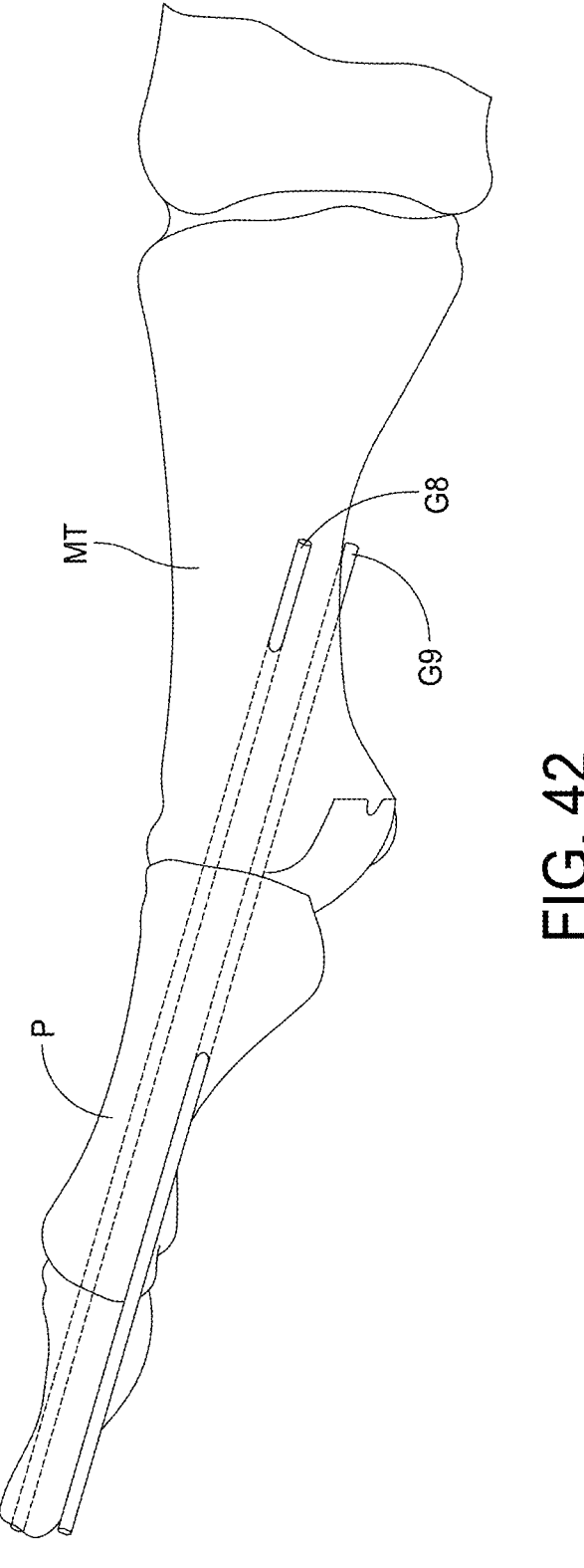
FIG. 42 shows guide wires in place.

With the fastener guide wires G8 and G9 placed, as shown in FIG. 42, the outrigger assembly 320 can be removed from the phalanx guide 314 while keeping the dorsal guide 310 in place (not shown for clarity). Depth gauging, pre-drilling, and driving the fixation fasteners can follow with the results like that shown, for example, in FIGS. 26A and 26B. After which, the dorsal guide 310 can be removed and the surgery completed.

It should be understood that the foregoing description is only illustrative of the inventions. Various alternatives and modifications can be devised by those skilled in the art without departing from the inventions. Accordingly, each invention is intended to embrace all such alternatives, modifications, and variances that fall within the scope of the appended claims.

What is claimed is:

1. A system for metatarsal phalangeal joint fusion comprising:
    a hinged guide including a connecting body coupled to a hinge body by a hinge so that the hinge body articulates with respect to the connecting body;
    a metatarsal guide attached to the hinge body; and
    a phalanx guide attached to the connecting body via a dowel and a lead screw;
    a trajectory guide attachable to the hinged guide; and
    an anchoring wire to attach the hinged guide to a bone.

2. The system of claim 1, wherein the hinged guide further includes:
    a first set screw to adjust articulation between the connecting body and the hinge body; and

13 a second set screw to adjust articulation between the hinge body and the metatarsal guide.

3. The system of claim 1, wherein the hinged guide includes radiopaque indicators.

4. The system of claim 2, wherein a distance between the connecting body and the phalanx guide is adjustable via the lead screw.

5. The system of claim 1, wherein the trajectory guide includes:

an upright portion that is insertable into the hinged guide; and an indicator portion that extends from the upright portion.

6. The system of claim 5, wherein the indicator portion includes a radiopaque indicator that extends from the upright portion.

7. The system of claim 1, further comprising a single-chamfer wire sleeve configured to be inserted through a hole in the trajectory guide along a trajectory for a fixation fastener.

8. The system of claim 1, wherein the hinged guide includes:

a connecting body;

a metatarsal guide attached by a hinge to the connecting body; and a phalanx guide attached to the connecting body via a dowel and a lead screw.

9. The system of claim 8, further comprising a first knob to lock articulation between the connecting body and the metatarsal guide.

10. The system of claim 8, further comprising:

two first converging anchoring wires insertable through the phalanx guide and into a phalanx; and two second converging anchoring wires insertable through the metatarsal guide and into a metatarsal.

11. The system of claim 8, further comprising an outrigger to attach the trajectory guide to the phalanx guide.

12. The system of claim 11, further comprising a second knob to lock articulation between the connecting body and the outrigger.

13. The system of claim 11, further comprising an adjustment screw to adjust elevation between the connecting body and the outrigger.

14

14. The system of claim 11, further comprising an outer single-chamfer wire sleeve configured to be inserted through a hole in the outrigger and anchored into a bone via a spike protruding from one end of the outer single-chamfer wire sleeve.

15. The system of claim 14, further comprising an inner single-chamfer wire sleeve configured to be inserted through a bore of the outer single-chamfer wire sleeve and guide a fastener guide wire into a bone.

16. The system of claim 14, wherein a bore through the outer single-chamfer wire sleeve is offset from a center of the outer single-chamfer wire sleeve.

17. A method of fusing a metatarsal phalangeal joint comprising:

aligning a hinged guide with a phalanx or a metatarsal;

anchoring the hinged guide to the phalanx or the metatarsal of the metatarsal phalangeal joint;

distracting the phalanx and the metatarsal;

preparing the metatarsal phalangeal joint;

adjusting dorsiflexion of the metatarsal phalangeal joint;

locking the hinged guide to set the dorsiflexion;

compressing the phalanx and the metatarsal;

selecting a trajectory of a fixation fastener; and inserting the fixation fastener into one of the phalanx and the metatarsal along a selected trajectory.

18. The method of claim 17, wherein the aligning includes placing a guide wire into about a center of a metatarsal head and placing the hinged guide over the guide wire.

19. The method of claim 17, wherein the anchoring includes placing a first wire through the hinged guide and into the phalanx and a second wire through the hinged guide and into the metatarsal.

20. The method of claim 17, wherein aligning the hinged guide includes visualizing radiopaque indicators in the hinged guide.

21. The method of claim 17, wherein the selecting a trajectory of a fixation fastener includes adjusting a trajectory guide with respect to the metatarsal phalangeal joint.

22. The method of claim 21, wherein the selecting a trajectory of a fixation fastener includes selecting a diameter of the fixation fastener.

* * * * *